(12) United States Patent
Foster et al.

(10) Patent No.: US 10,660,854 B2
(45) Date of Patent: May 26, 2020

(54) THERMOSTABLE VACCINES BASED ON ETHER LIPIDS AND NATIVE VIRAL ENVELOPE PROTEINS

(71) Applicant: Batavia Biosciences Inc., Woburn, MA (US)

(72) Inventors: David Foster, North Uxbridge, MA (US); Menzo Jans Emco Havenga, Leiden (NL)

(73) Assignee: Batavia Biosciences Inc., Woburn, MA (US)

( * ) Notice: Subject to any disclaimer, the term of this patent is extended or adjusted under 35 U.S.C. 154(b) by 0 days.

(21) Appl. No.: 15/813,706

(22) Filed: Nov. 15, 2017

(65) Prior Publication Data

US 2018/0085313 A1    Mar. 29, 2018

Related U.S. Application Data

(63) Continuation of application No. PCT/US2016/032703, filed on May 16, 2016.

(60) Provisional application No. 62/162,704, filed on May 16, 2015.

(51) Int. Cl.

| | | |
|---|---|---|
| *A61K 9/127* | (2006.01) | |
| *A61K 39/12* | (2006.01) | |
| *C12N 7/00* | (2006.01) | |
| *C07K 17/04* | (2006.01) | |
| *C07K 14/775* | (2006.01) | |
| *A61K 47/28* | (2006.01) | |
| *A61K 9/00* | (2006.01) | |
| *C07K 17/00* | (2006.01) | |
| *A61K 39/215* | (2006.01) | |
| *A61K 39/205* | (2006.01) | |
| *A61K 39/155* | (2006.01) | |
| *A61K 39/145* | (2006.01) | |
| *A61K 39/245* | (2006.01) | |
| *A61K 39/275* | (2006.01) | |
| *A61K 39/29* | (2006.01) | |
| *C07K 14/005* | (2006.01) | |
| *C12N 15/87* | (2006.01) | |
| *A61K 39/00* | (2006.01) | |
| *B82Y 5/00* | (2011.01) | |

(52) U.S. Cl.
CPC .......... *A61K 9/1272* (2013.01); *A61K 9/0019* (2013.01); *A61K 9/1274* (2013.01); *A61K 39/12* (2013.01); *A61K 39/145* (2013.01); *A61K 39/155* (2013.01); *A61K 39/205* (2013.01); *A61K 39/215* (2013.01); *A61K 39/245* (2013.01); *A61K 39/275* (2013.01); *A61K 39/29* (2013.01); *A61K 47/28* (2013.01); *C07K 14/005* (2013.01); *C07K 14/775* (2013.01); *C07K 17/00* (2013.01); *C07K 17/04* (2013.01); *C12N 7/00* (2013.01); *C12N 15/87* (2013.01); *A61K 2039/5258* (2013.01); *A61K 2039/55516* (2013.01); *A61K 2039/55555* (2013.01); *A61K 2039/6018* (2013.01); *B82Y 5/00* (2013.01); *C12N 2710/16034* (2013.01); *C12N 2710/16071* (2013.01); *C12N 2710/24034* (2013.01); *C12N 2710/24071* (2013.01); *C12N 2730/10034* (2013.01); *C12N 2730/10071* (2013.01); *C12N 2760/14123* (2013.01); *C12N 2760/14134* (2013.01); *C12N 2760/14152* (2013.01); *C12N 2760/14171* (2013.01); *C12N 2760/16034* (2013.01); *C12N 2760/16071* (2013.01); *C12N 2770/24134* (2013.01); *C12N 2770/24171* (2013.01); *Y02A 50/392* (2018.01)

(58) Field of Classification Search
CPC .. A61K 9/1272; A61K 39/215; A61K 39/205; A61K 39/155; A61K 39/145; A61K 39/245; A61K 39/275; A61K 39/29; A61K 39/12; A61K 2039/6018; A61K 2039/55555; C07K 17/00; C07K 14/775
See application file for complete search history.

(56) References Cited

U.S. PATENT DOCUMENTS

| | | |
|---|---|---|
| 7,048,949 B2 | 5/2006 | Sligar |
| 7,083,958 B2 | 8/2006 | Sligar |
| 7,575,763 B2 | 8/2009 | Sligar |
| 7,592,008 B2 | 9/2009 | Sligar |
| 7,622,437 B2 | 11/2009 | Morrissey |
| 7,662,410 B2 | 2/2010 | Sligar |
| 7,691,414 B2 | 4/2010 | Sligar |
| 10,060,924 B2 * | 8/2018 | Ulbert .................. C07K 14/005 |

(Continued)

OTHER PUBLICATIONS

Bhattacharya, P., et al., Jan. 2010, Nanodisc-incorporated hemagglutinin provides protective immunity against influenza virus infection, J. Virol. 84(1):361-371.*

(Continued)

*Primary Examiner* — Jeffrey S Parkin
(74) *Attorney, Agent, or Firm* — Stradley Ronon Stevens & Young, LLP

(57) ABSTRACT

A platform enabling the manufacture of thermostable vaccines by incorporating recombinantly expressed, viral envelope proteins in their native conformation into ether glycerophospholipid nanodisc structures that simulate the natural environment of the envelope proteins. The ether glycerophospholipids include ether-linked hydrophobic side chains, and are derived from or modeled after those found in thermophile bacteria, which increase thermostability, thereby significantly enhancing the vaccine's potency, enabling the production of highly multivalent vaccines incorporating multiple variants of the viral antigen, and improving stability and shelf-life.

18 Claims, 18 Drawing Sheets

Specification includes a Sequence Listing.

(56) References Cited

U.S. PATENT DOCUMENTS

| | | |
|---|---|---|
| 2005/0182243 A1 | 8/2005 | Sligar |
| 2012/0156672 A1 | 6/2012 | Otte |
| 2013/0023695 A1 | 1/2013 | Kashiwaba |
| 2013/0157312 A1 | 6/2013 | Otte |

OTHER PUBLICATIONS

Midtgaard, S. R., et al., 2014, Self-assembling peptide form nanodiscs that stabilize membrane proteins, Soft Matter 10:738-752.*

Awasthi, S., et al., 2014, Improving immunogenicity and efficacy of vaccines for genital herpes containing herpes simplex virus glycoprotein D, Exp. Rev. Vaccines 13(12):1475-1488.*

Ye, L., et al., 2006, Ebola virus-like particles produced in insect cells exhibit dendritic cell stimulating activity and induce neutralizing antibodies, Virol. 351:260-270.*

Bayburt et al., "Membrane protein assembly into Nanodiscs", FEBS Lett, 2010, 584, pp. 1721-1727.

Bhattacharya et al., "Nanodisc-Incorporated Hemagglutinin Provides Protective Immunity against Influenza Virus Infection", Journal of Virology, 2010, 84(1), pp. 361-371.

Chong et al., "Archaebacterial bipolar tetraether lipids: Physicochemical and membrane properties", Chemistry and Physics of Lipids, 2010, 163(3), pp. 253-265.

Nakatani-Webster et al., "Assembly and characterization of gp160-nanodiscs: A new platform for biochemical characterization of HIV envelope spikes", . J Virol Methods, 2015, 226, pp. 15-24.

Swenson et al., "Virus-like particles exhibit potential as a pan-filovirus vaccine for both Ebola and Marburg viral infections", Vaccine, 2005, 23(23), pp. 3033-3042.

\* cited by examiner

| rHA Nanodiscs | Mol wt. | log (Mw) | Calculated Ve |
|---|---|---|---|
| 1 rHA per ND | 220880 | 5.3441564 | 15.015 |
| 2 rHA per ND | 292800 | 5.4665711 | 14.668 |
| 3 rHA per ND | 364800 | 5.5620548 | 14.397 |

| Peak | Retention (ml) | $K_{av}$ | Mol wt. | log (Mw) |
|---|---|---|---|---|
| Thyroglobulin | 13.063 | 0.33 | 670000 | 5.8260748 |
| y-globulin | 16.012 | 0.51 | 158000 | 5.1986571 |
| Ovalbumin | 17.345 | 0.60 | 44000 | 4.6434527 |
| Myoglobin | 18.468 | 0.67 | 17000 | 4.2304489 |
| Vitamin B12 | 20.671 | 0.81 | 1350 | 3.1303338 |

| Fraction | Conc. (mg/ml) | Amount (mg) | V (ml) |
|---|---|---|---|
| B1 | 0.007 | 0.004 | 11.865 |
| B2 | 0.010 | 0.005 | 12.365 |
| B3 | 0.012 | 0.006 | 12.865 |
| B4 | 0.013 | 0.007 | 13.160 |
| B5 | 0.013 | 0.007 | 13.866 |
| B6 | 0.015 | 0.007 | 14.366 |
| B7 | 0.018 | 0.009 | 14.865 |
| B8 | 0.024 | 0.012 | 15.365 |
| B9 | 0.057 | 0.029 | 15.865 |
| B10 | 0.204 | 0.102 | 16.366 |
| B11 | 0.341 | 0.170 | 16.755 |

| Fraction | Conc (mg/ml) | Amount (mg) | V (ml) |
|---|---|---|---|
| B1 | 0.011 | 0.006 | 11.868 |
| B2 | 0.013 | 0.007 | 12.368 |
| B3 | 0.014 | 0.007 | 12.691 |
| B4 | 0.014 | 0.007 | 12.889 |
| B5 | 0.013 | 0.007 | 13.367 |
| B6 | 0.014 | 0.007 | 14.369 |
| B7 | 0.017 | 0.008 | 14.869 |
| B8 | 0.021 | 0.011 | 15.369 |
| B9 | 0.044 | 0.022 | 15.869 |
| B10 | 0.117 | 0.059 | 16.368 |
| B11 | 0.181 | 0.091 | 16.721 |

THERMOSTABLE VACCINES BASED ON ETHER LIPIDS AND NATIVE VIRAL ENVELOPE PROTEINS

CROSS-REFERENCE TO RELATED APPLICATIONS

This application is a continuation-in-part of PCT Application No. PCT/US2016/032703, filed May 16, 2016, which claims priority to U.S. Provisional Application No. 62/162,704, filed May 16, 2015, the contents of which are incorporated by reference herein, in their entirety and for all purposes.

REFERENCE TO SEQUENCE LISTING

This application includes a Sequence Listing submitted electronically as a text file named 18804500101SEQ, created on Nov. 15, 2017 with a size of 45 kilobytes. The Sequence Listing is incorporated by reference herein.

FIELD

The present disclosure relates generally to the field of vaccine manufacture. More particularly, the present disclosure relates to nanodisc carriers for vaccine antigens, which comprise a bilayer of thermostable phospholipids comprising ether linkages between the phosphate and hydrophobic side chains, scaffold proteins, and viral envelope protein antigens in their native conformation embedded within the carrier.

BACKGROUND

Various publications, including patents, published applications, accession numbers, technical articles and scholarly articles are cited throughout the specification. Each of these cited publications is incorporated by reference, in its entirety and for all purposes, in this document.

Classical methods of vaccine production use either modified live (e.g., attenuated) virus or killed (e.g., inactivated) virus to stimulate immunity. The development and accelerated production of safer and more stable vaccines is desirable for combatting highly virulent pathogens of interest. In addition, vaccines that are thermo-stable are needed for use and distribution in areas of the world where refrigeration is scarce and supplies must be stored in unregulated conditions where temperatures are well in excess of that required to maintain the potency of typical vaccine formulations. An example of the urgent need for such thermo-stable vaccines has been the Ebola outbreak in towns and remote villages of Africa.

Ebola virus (EBOV), a member of the order of enveloped viruses Mononegavirales, causes a severe hemorrhagic disease in humans, exhibiting mortality rates as high as 90%.1 This high mortality rate, combined with an absence of efficacious treatments or established vaccination options, makes Ebola virus a critical public health pathogen, and a bio threat pathogen of category A.

The EBOV surface glycoprotein (GP) mediates attachment to and fusion of the virus with host cells. GP is a type 1 transmembrane protein that is displayed on the virion envelope as a homo-trimeric spike, similar in fashion to several other envelope antigens (e.g., HIV Env and influenza virus hemagglutinin (HA)). The GP protein is exposed on the surface of Ebola virions, and it is widely recognized as the primary antigen of Ebola—thus vaccination with a purified, native-like but noninfectious protein is an obvious choice for an effective vaccination strategy.

The extracellular domain of the Zaire Ebola virus (ZEBOV) GP protein, lacking its transmembrane domain, has been fused to the Fc fragment of human IgG1 and the resultant fusion protein was successfully expressed in mammalian cells. Although this sort of soluble construct conferred protection to mice against a lethal viral challenge, it failed when similarly tested in non-human primates (NHP). Vaccines that utilize soluble forms of virion envelope antigens may not properly mimic the native structure of the membrane-integrated glycoprotein displayed on the virion for the purpose of immunization. This perspective is supported by studies in which antigens expressed in their native conformation are more effective at eliciting an effective immune response than in their non-native form. Indeed, virus-like particles (VLP) that present full-length, native GP on their surfaces have recently been demonstrated to be efficacious in eliciting protective immunity in NHP.

Although VLPs can be produced by transfecting mammalian cell lines with the EBOV matrix protein (VP40) and GP, VLPs are less than ideal vaccines for a number of reasons. Primarily, they are particulate in nature, and thus impossible to separate from other particulate contaminants like adventitious viruses. Because they have enclosed spaces it is exceedingly difficult to ensure the complete removal or inactivation of endogenous host nucleic acids or entrapped host proteins. Since the envelopes of VLPs are derived from the membrane of the host cell that produces them, they consequently contain many additional membrane-anchored or membrane-integrated proteins originating from the host cell membrane. Yet the success of using Ebola VLPs to elicit effective immune responses in NHP suggests that if envelope antigens could be highly purified and delivered in a vaccine in their native, membrane-embedded form, just as they are in VLPs, they may be equally effective in promoting protective immunity.

If envelope antigens could be delivered in a vehicle with built-in adjuvant properties, they might even prove more effective, and without the drawbacks of VLPs with respect to contamination with host-derived or potentially infectious, adventitious contaminants.

SUMMARY

A thermostable vaccine carrier comprises a bilayer comprising one or more ether glycerophospholipids and one or more membrane scaffold proteins self-assembled into a nanodisc, and a microbial protein antigen embedded into the nanodisc. The one or more ether glycerophospholipids may comprise 1,2-di-O-phytanyl-sn-glycero-3-phosphocholine, 1,2-di-O-phytanyl-sn-glycerol, 1,2-di-O-phytanyl-sn-glycerol, 1,2-di-O-phytanyl-sn-glycero-3-phosphoethanolamine, glycerol dialkyl glycerol tetraether, 1,2-di-O-octadecyl-sn-glycero-3-phosphocholine, 1,2-di-O-(9Z-octadecenyl)-sn-glycero-3-phosphocholine, 2-3-diphytanyl-O-sn-glycerol (archaeol), caldarcheol, isocalarcheol, gentiobiosyl archaeol, archaetidylethanoloamine, or gentyobiosyl caldarchaetidylethanoloamine, or any combinations thereof. The membrane scaffold protein may comprise a polypeptide fragment of human apolipoprotein A1, or a variant thereof having one amino acid substitution or deletion. The membrane scaffold protein may comprise one or more of the amino acid sequence of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13.

The microbial protein antigen may comprise a virus envelope protein. The virus envelope protein may be from a DNA virus or an RNA virus. The virus envelope protein may be purified from a virus-like particle (VLP) as described herein. The DNA virus may be a herpesvirus, a poxvirus, or a hepadnavirus. The RNA virus may be a togavirus, a coronavirus, an orthomyxovirus such as Influenza Type A, Influenza Type B, or Influenza Type C, a paramyxovirus, a rhabdovirus, a bunyavirus, a filovirus such as the Ebola virus, or a flavivirus such as the Zika virus. Preferred envelope proteins include the Influenza hemagglutinin protein (e.g., the amino acid sequence of SEQ ID NO:18), the Ebola VP40 protein (e.g., the amino acid sequence of SEQ ID NO:15), the Ebola GP protein (e.g., the amino acid sequence of SEQ ID NO:16), and the Zika virus envelope protein (e.g., the amino acid sequence of SEQ ID NO:17).

A composition comprises a thermostable vaccine carrier such as those described above, and a pharmaceutically acceptable carrier. The composition may further comprise a pharmaceutically acceptable excipient and/or an adjuvant.

A kit comprises a thermostable vaccine carrier or composition thereof such as those described above, and instructions for using the carrier in a method for vaccinating a subject in need thereof. The kit may comprise a container such as a syringe or diluent bag, and optionally comprise a needle or catheter for administering the thermostable vaccine carrier or composition to a subject.

A method for vaccinating a subject comprises administering to the subject a thermostable vaccine carrier or composition thereof such as those described above, in an amount effective to confer an immune response in/by the subject against the microbial protein antigen. Administration may be by injection. The injection may be a subcutaneous, intramuscular, or intravenous injection.

A thermostable vaccine carrier or composition thereof such as those described above may be used in the manufacture of a medicament or a vaccine. A thermostable vaccine carrier or composition thereof such as those described above may be used in the treatment or prevention of a virus infection or in the manufacture of a medicament or a vaccine for the treatment or prevention of a virus infection. A thermostable vaccine carrier or composition thereof such as those described above may be used in the treatment or prevention of a herpesvirus infection, a poxvirus infection, a hepadnavirus infection, a togavirus infection, a coronavirus infection, an orthomyxovirus infection, a paramyxovirus infection, a rhabdovirus infection, a bunyavirus infection, a filovirus infection, or a flavivirus infection. A thermostable vaccine carrier or composition thereof such as those described above may be used in the treatment or prevention of an Ebola virus infection. A thermostable vaccine carrier or composition thereof such as those described above may be used in the treatment or prevention of a Zika virus infection. A thermostable vaccine carrier or composition thereof such as those described above may be used in the treatment or prevention of an Influenza virus infection.

A method for making a thermostable vaccine carrier such as those described above comprise mixing one or more ether glycerophospholipids, one or more membrane scaffold proteins, and one or more microbial protein antigens in an aqueous media comprising a detergent, removing the detergent, and allowing the one or more membrane scaffold proteins and the one or more ether glycerophospholipids to self-assemble into the nanodisc having the one or more microbial protein antigen embedded therein. The method may further comprise lyophilizing the nanodisc.

A process for producing substantially pure Ebola GP protein comprises transfecting Ebola VP40 protein-expressing stable cells with a gene encoding the Ebola GP protein, isolating virus-like particles comprising the Ebola VP40 protein and Ebola GP protein produced from the transfected cells, separating the GP protein from the VP40 protein, and purifying the separated GP protein. The stable cells may be Chinese Hamster Ovary (CHO) cells or Human Embryonic Kidney 293 (HEK 293) cells.

Figure 9:
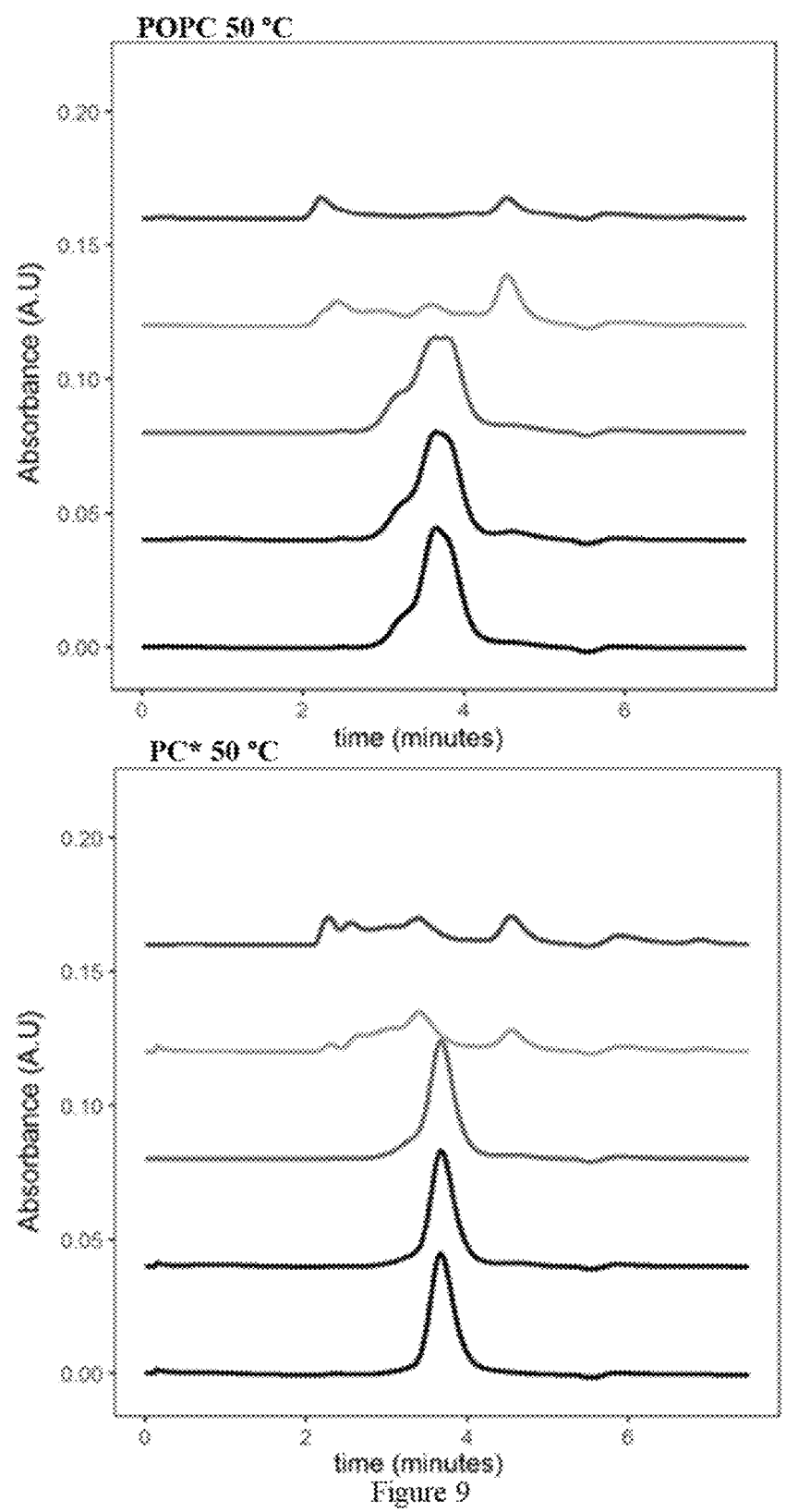

FIG. 9 shows size exclusion chromatography plots from thermostability testing of glycerophospholipid POPC and PC* nanodiscs at 50 degrees C. over the indicated time periods of (from top to bottom) 48 hours, 24 hours, 120 minutes, 60 minutes, and 30 minutes. POPC plots are shown in the left panel and PC* plots are shown in the right panel.

Figure 10:
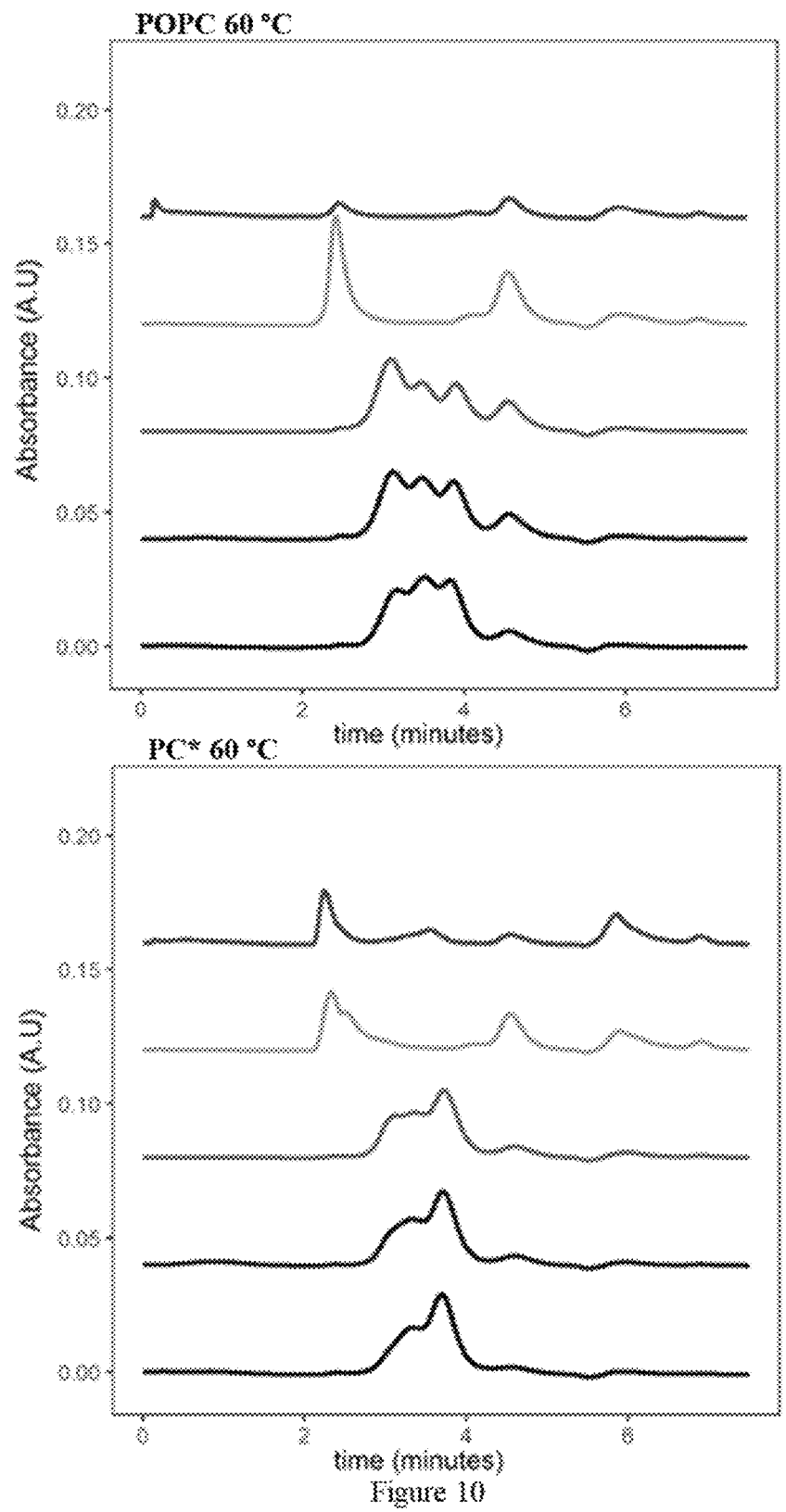

FIG. 10 shows size exclusion chromatography plots from thermostability testing of glycerophospholipid POPC and PC* nanodiscs at 60 degrees C. over the indicated time periods of (from top to bottom) 48 hours, 24 hours, 120 minutes, 60 minutes, and 30 minutes. POPC plots are shown in the left panel and PC* plots are shown in the right panel.

Figure 11:
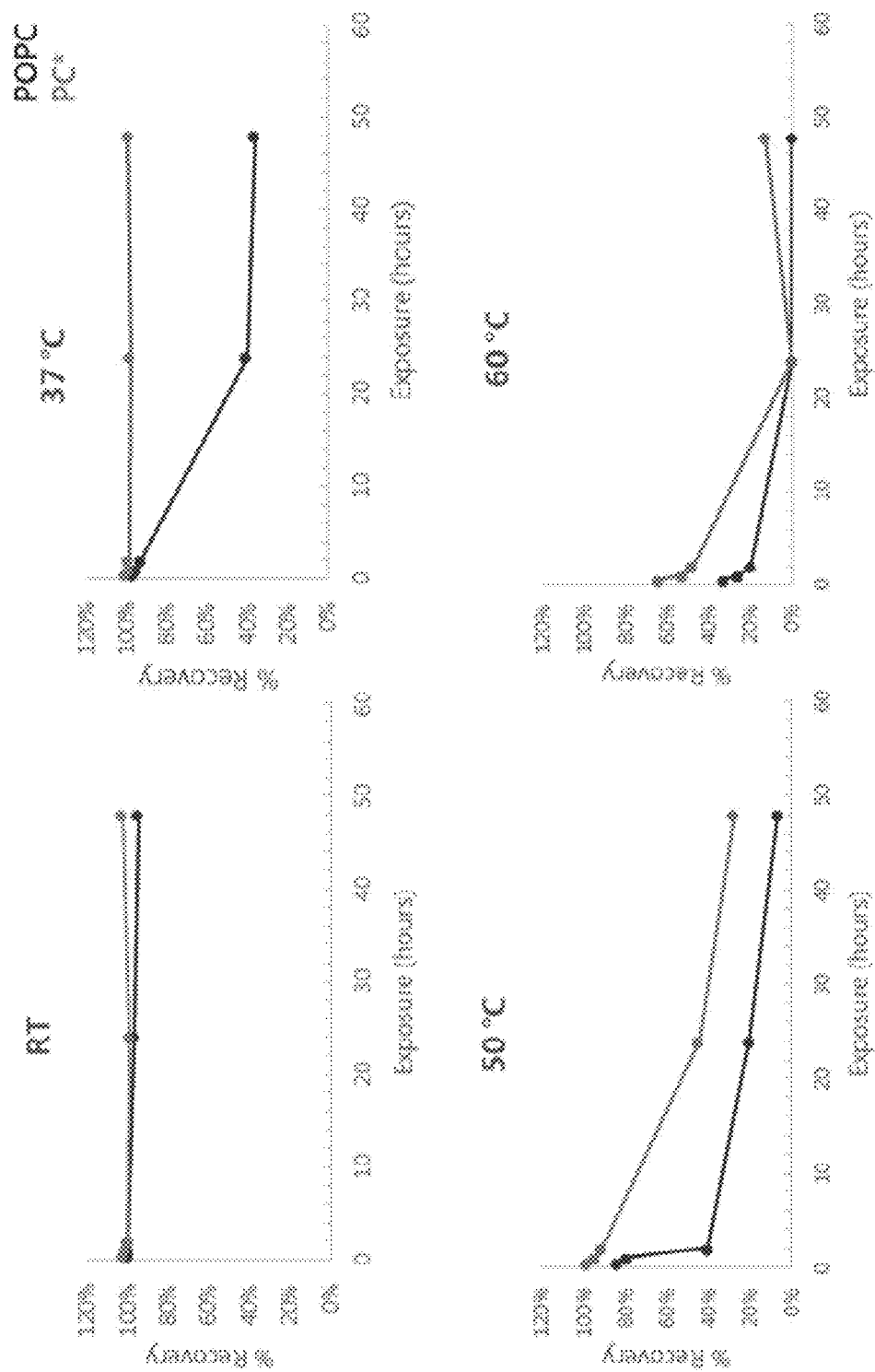

FIG. 11 shows the percent recovery of glycerophospholipid POPC and PC* nanodiscs over time, based on thermostability testing by SE-HPLC peak area. The top left quadrant shows the plot for room temperature, the top right quadrant shows the plot for 37 degrees C., the bottom left quadrant shows the plot for 50 degrees C., and the bottom right quadrant shows the plot for 60 degrees C. In each plot, the top-most line (lighter gray line) shows data for PC* nanodiscs, and the bottom-most line (darker gray line) shows data for POPC nanodiscs.

Figure 12:
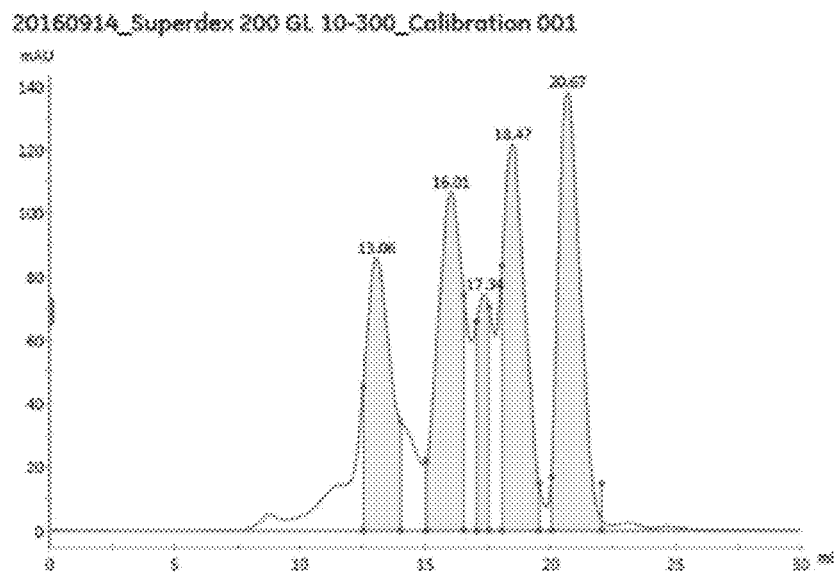
Figure 12:
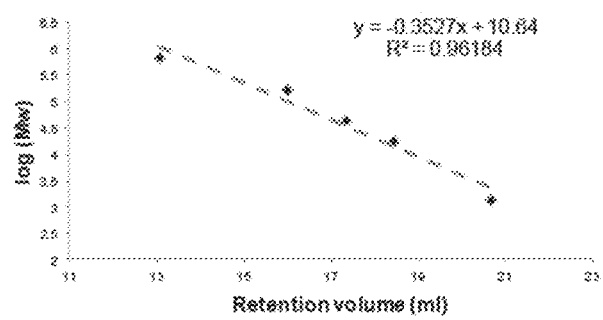

FIG. 12 shows theoretical retention volumes of three species on a Superdex 200 Increase 10-300 GL size exclusion chromatography (SEC) column.

Figure 13:
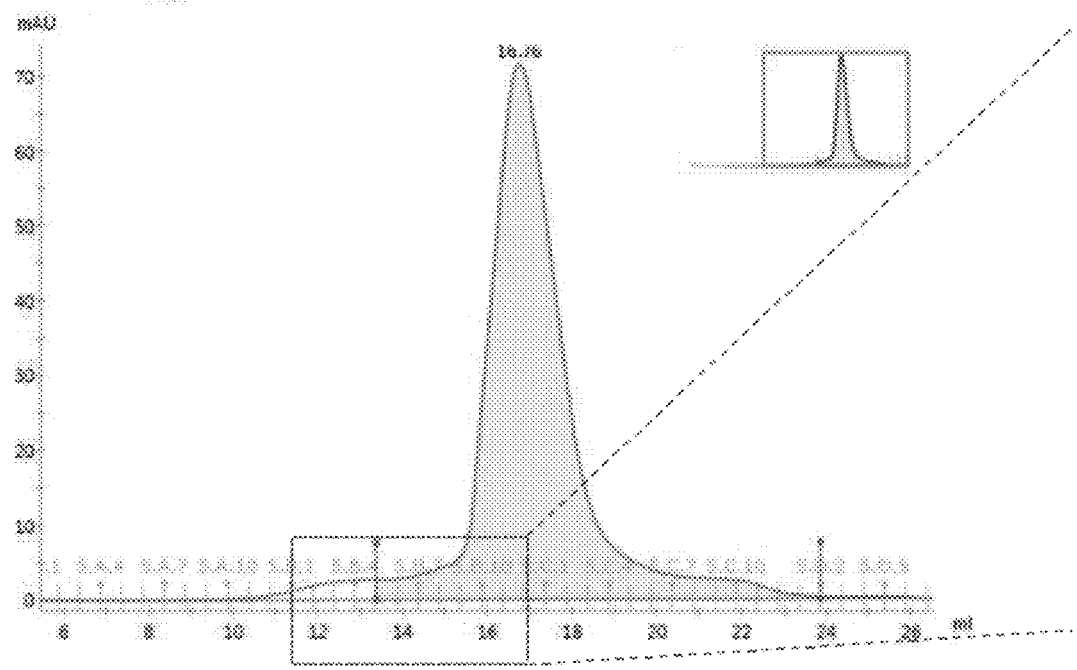

FIG. 13 shows an SEC chromatogram of the rHA-Nanodisc mixture.

Figure 14:
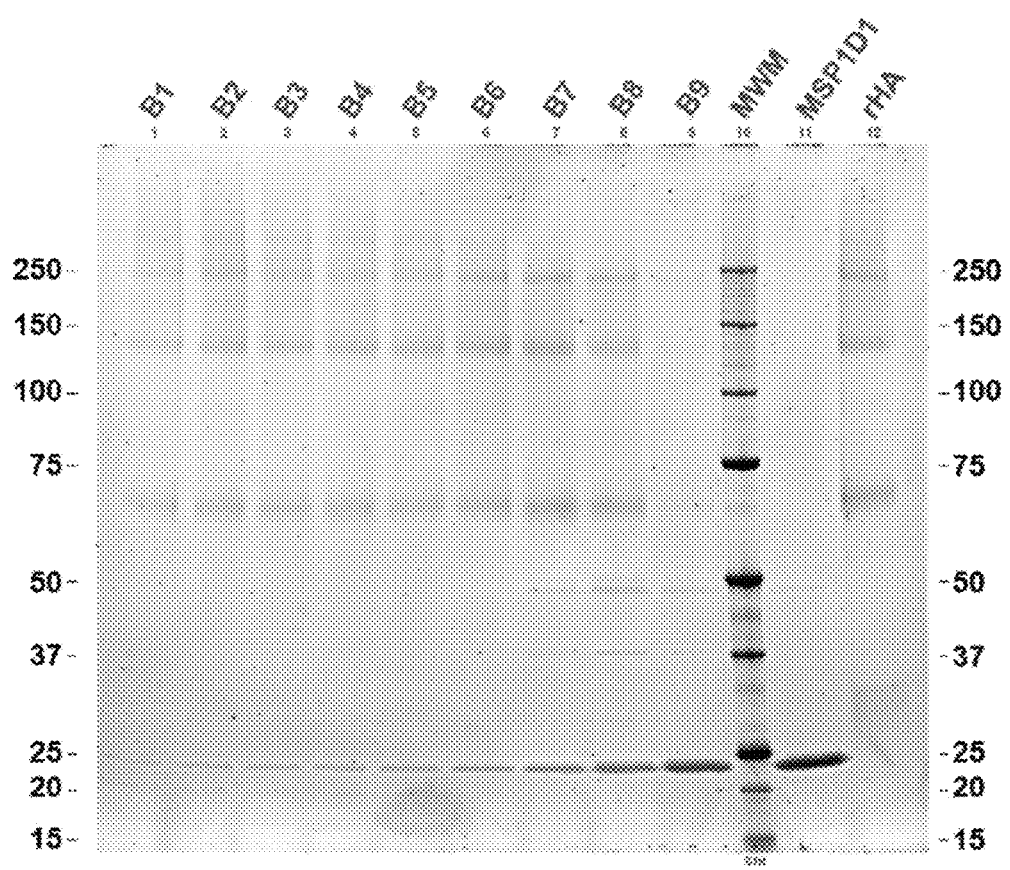

FIG. 14 shows an SDS PAGE gel of SEC fractions from rHA Nanodisc purification.

Figure 15:
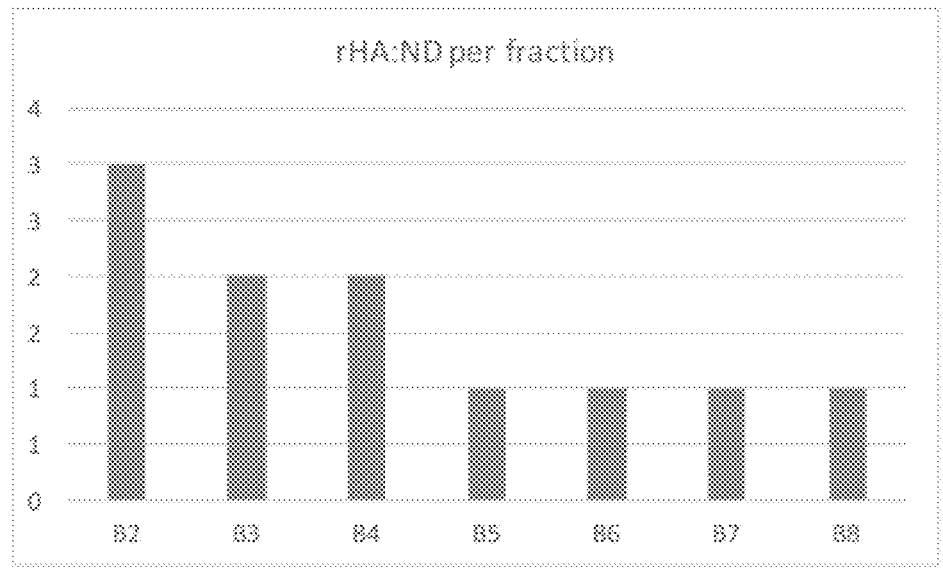

FIG. 15 shows the results set forth in FIG. 14 pictorially.

Figure 16:
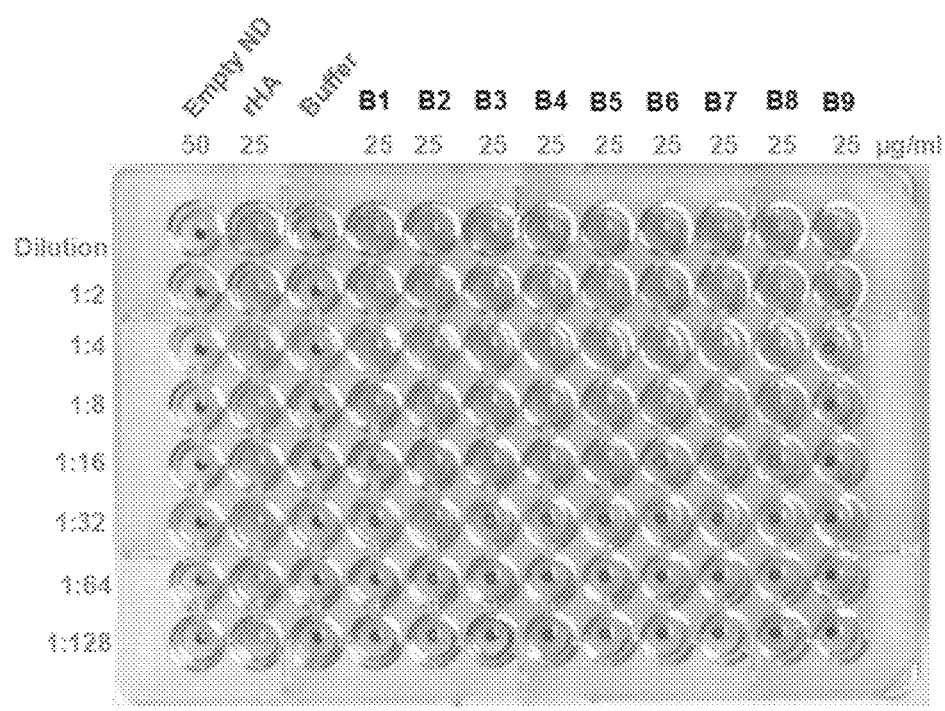

FIG. 16 shows hemagglutination results.

Figure 17:
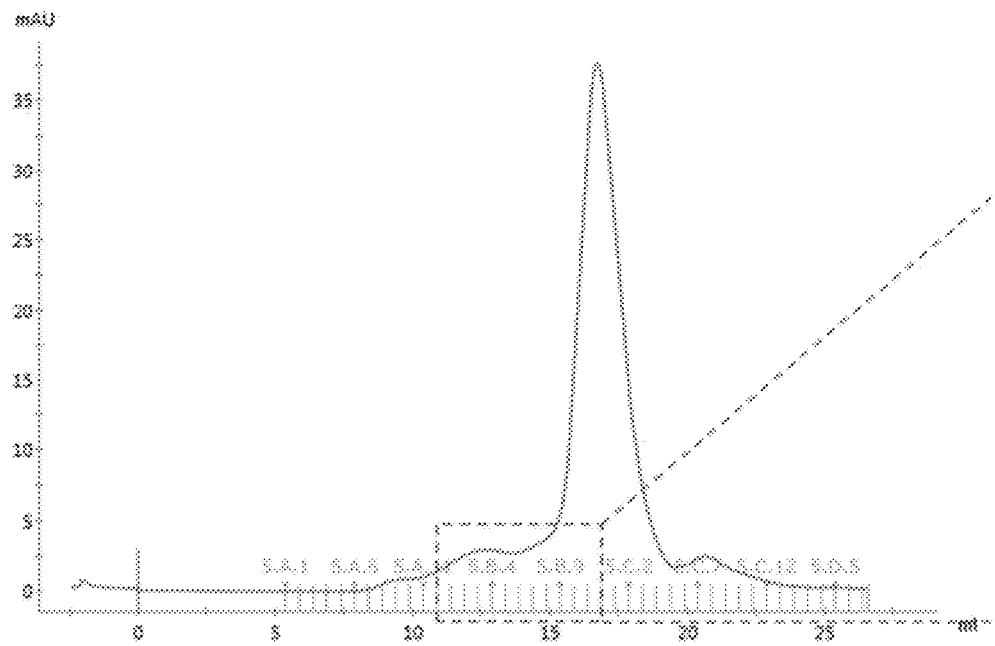

FIG. 17 shows an SEC chromatogram of the rHA-Nanodisc mixture.

Figure 18:
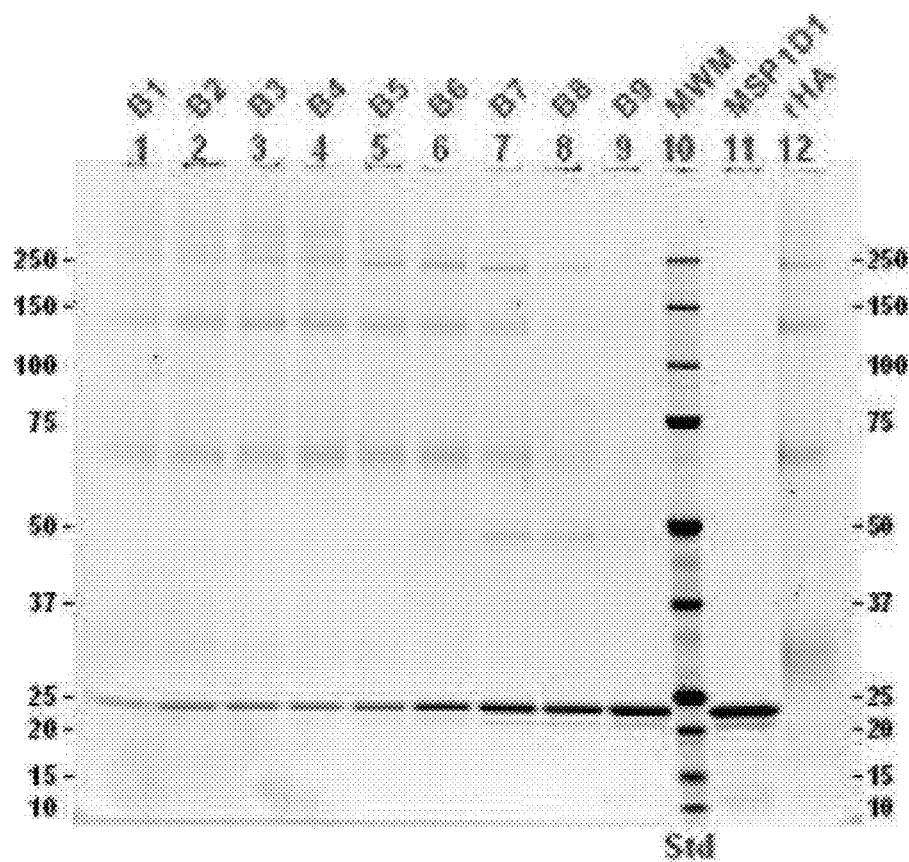

FIG. 18 shows an SDS PAGE gel of SEC fractions from rHA Nanodisc purification.

Figure 19:
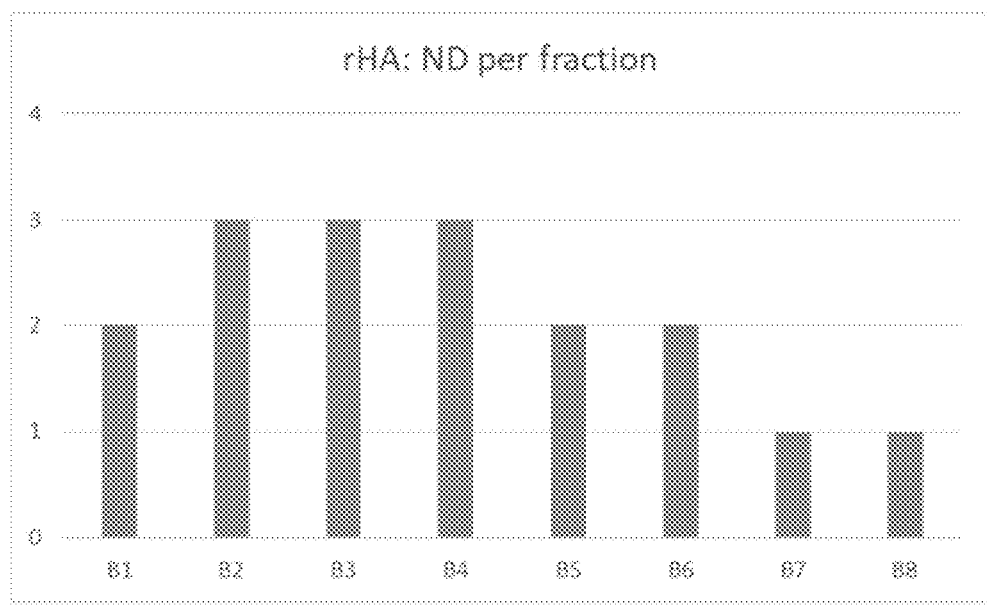

FIG. 19 shows the results set forth in FIG. 18 pictorially.

DETAILED DESCRIPTION

Various terms relating to aspects of the present disclosure are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

The terms subject and patient are used interchangeably. A subject may be any animal, and preferably is a mammal. A mammalian subject may be a farm animal (e.g., sheep, horse, cow, pig), a companion animal (e.g., cat, dog), a rodent or laboratory animal (e.g., mouse, rat, rabbit), or a non-human primate (e.g., old world monkey, new world monkey). Human beings are highly preferred.

A "phospholipid" includes a phosphate group joined to one or more, including two, hydrocarbon tails, which are typically long fatty acid chains that may be saturated or unsaturated. The phosphate group may further be joined to any suitable substituent group such as a choline, ethanolamine, glycerol, inositol, or serine. "Glycerophospholipids" are phospholipids including a glycerol group between the phosphate and two hydrocarbon tails (e.g., long fatty acid chains that may be saturated or unsaturated). "Ether phospholipids" include "ether glycerophospholipids," in which one or more of the carbons on the glycerol group are joined to a hydrocarbon tail via an ether linkage.

A "nanodisc" comprises a bilayer of phospholipids, preferably glycerophospholipids and more preferably ether glycerophospholipids and one or more membrane scaffold proteins or peptides that form a belt-like perimeter around the hydrophobic edges of the bilayer (e.g., FIG. 1).

It was observed in accordance with the present disclosure that ether glycerophospholipids, together with membrane scaffold proteins, can be used to form nanodisc vaccine carriers. The nanodisc vaccine carriers self-assemble under aqueous conditions, and can be loaded with vaccine antigens, and administered to a subject as part of a vaccine in order to elicit a protective immune response. It was further observed that the use ether glycerophospholipids increases the thermostability of the nanodisc carrier relative to ester glycerophospholipids. It is believed that the presence of the ether linkage instead of the ester linkage significantly enhances the stability and shelf-life of the nanodisc structure, and further enhances the potency and efficacy of the vaccine that is administered, particularly in view of the immunogenic and potent adjuvant properties associated with archaebacterial/thermophilic bacterial lipids.

The nanodiscs prepared according to the present disclosure enable manufacturing of thermostable vaccines by incorporating viral envelope proteins in their native, substantially non-denatured conformation into the nanodiscs, providing for both thermostability and high immunogenicity. The present disclosure provides a highly extensible means to rapidly (within a few months) manufacture thermostable, potent vaccines to defend against infectious enveloped viruses, and uniquely provides the potential to be quickly reconfigured to incorporate new or altered antigens on very short notice. The present disclosure further enables the creation of highly multivalent configurations to adapt to rapidly changing antigen epitopes or multiple emergent bio threats.

The present disclosure presents several highly advantageous features to facilitate immunization against infectious agents, particularly enveloped viruses. Such advantageous features include, but are not limited to: The capacity to manufacture a vaccine using high cell mass electroporation to rapidly introduce the target envelope protein into VLPs, which can be purified and then used to extract the glycoprotein, then reconstitute it into nanodiscs of relatively standardized composition; The potency anticipated for nanodiscs incorporating archaebacterial lipids with adjuvant properties enables the incorporation of multiple DNA sequences in the transient transfection, permitting the manufacture of multivalent vaccines; The use of thermostable lipids confers thermostability to the nanodiscs, enabling the storage, shipment, and deployment of nanodisc-based vaccines in the field without the necessity for cryogenic or refrigerated storage; and the capacity to modify to develop and manufacture vaccines capable of inducing protective immunity to a wide variety of dangerously infectious enveloped vaccines.

Thus, in some embodiments, the present disclosure provides ether glycerophospholipid nanodiscs. The ether glycerophospholipid nanodiscs may be used, for example, as a carrier for vaccine antigens, and may provide the additional benefit of functioning as an adjuvant in a vaccine preparation. The ether glycerophospholipid nanodiscs are thermostable, particularly at elevated temperatures (e.g., those above room temperature, including temperatures at or above the temperature of the human body, 37 degrees C.). The ether glycerophospholipid nanodiscs are more thermostable than ester glycerophospholipid nanodiscs. Thus, the ether glycerophospholipid nanodiscs provide an improvement over the nanoscale particles described in U.S. Pat. No. 7,691,414, U.S. Pat. No. 7,662,410, U.S. Pat. No. 7,622,437, U.S. Pat. No. 7,592,008, U.S. Pat. No. 7,547,5763, U.S. Pat. No. 7,083,958, and U.S. Pat. No. 7,048,949.

In some embodiments, a thermostable vaccine carrier comprises a bilayer comprising one or more ether glycerophospholipids and one or more membrane scaffold proteins self-assembled into a nanodisc, and a microbial protein antigen embedded into the nanodisc. The ether glycerophospholipids may comprise any suitable ether glycerophospholipids that are found in the cell membrane of archaebacteria, particularly thermophilic archaebacteria. The ether glycerophospholipids may be synthetic. In some embodiments, ether glycerophospholipids that are found in the cell membrane of archaebacteria and synthetic ether glycerophospholipids may be used in combination. Non-limiting examples of suitable ether glycerophospholipids include 1,2-di-O-phytanyl-sn-glycero-3-phosphocholine, 1,2-di-O-phytanyl-sn-glycero-3-phosphoethanolamine, 1,2-di-O-phytanyl-sn-glycerol, glycerol dialkyl glycerol tetraether, 1,2-di-O-octadecyl-sn-glycero-3-phosphocholine, 1,2-di-O-(9Z-octadecenyl)-sn-glycero-3-phosphocholine, 2-3-diphytanyl-O-sn-glycerol (archaeol), caldarcheol, isocalarcheol, gentiobiosyl archaeol, archaetidylethanoloamine, gentyobiosyl caldarc haetidylethanoloamine, and any combination thereof.

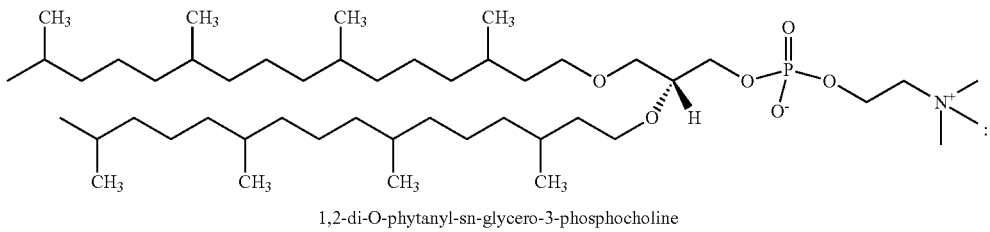

1,2-di-O-phytanyl-sn-glycero-3-phosphocholine

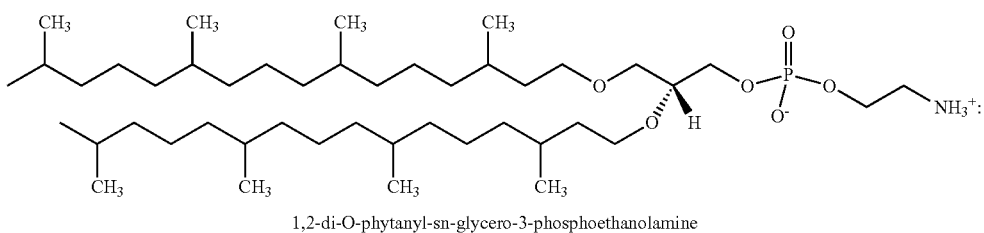

1,2-di-O-phytanyl-sn-glycero-3-phosphoethanolamine

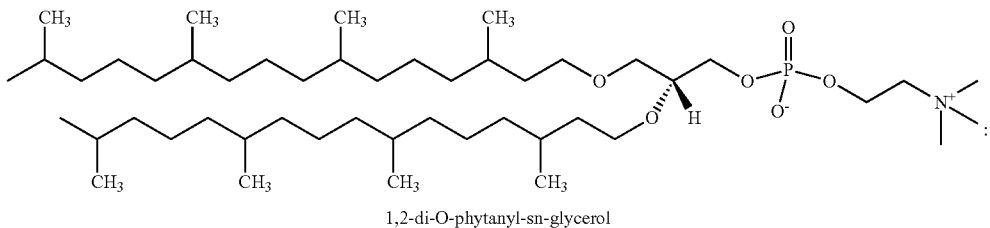

1,2-di-O-phytanyl-sn-glycerol

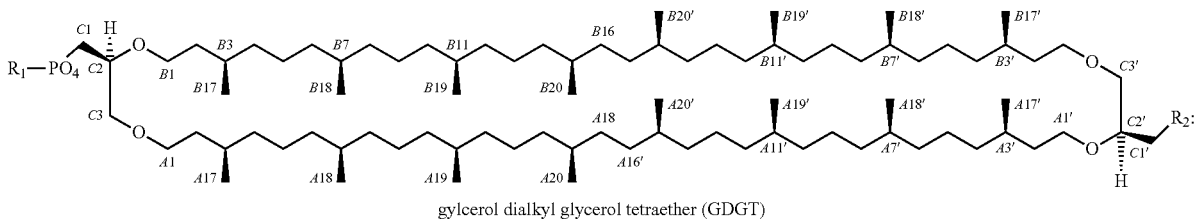

gylcerol dialkyl glycerol tetraether (GDGT)

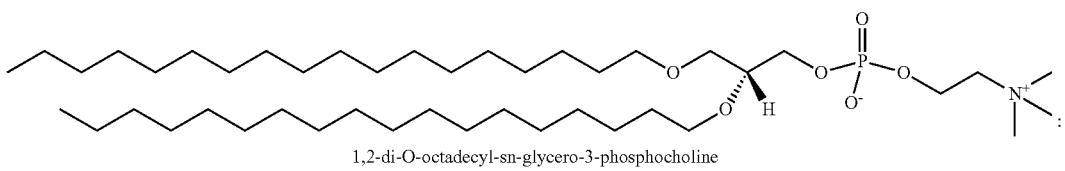

1,2-di-O-octadecyl-sn-glycero-3-phosphocholine

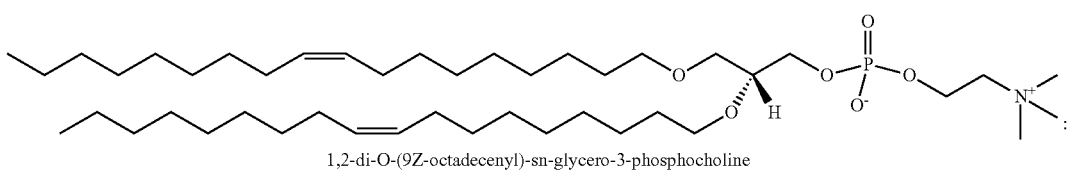

1,2-di-O-(9Z-octadecenyl)-sn-glycero-3-phosphocholine

-continued
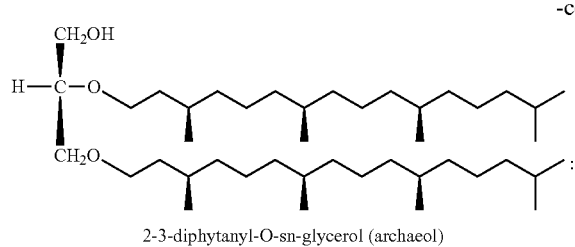
2-3-diphytanyl-O-sn-glycerol (archaeol)
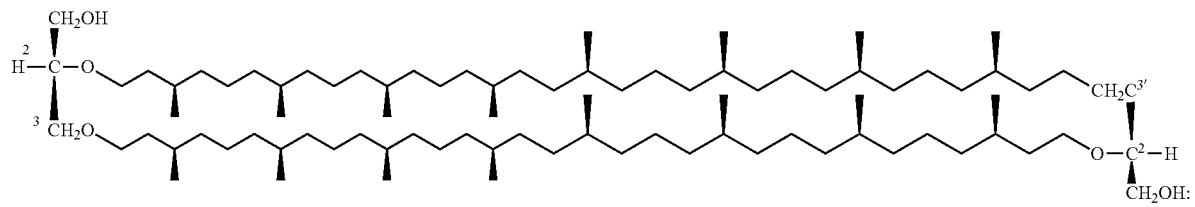
Caldarcheol
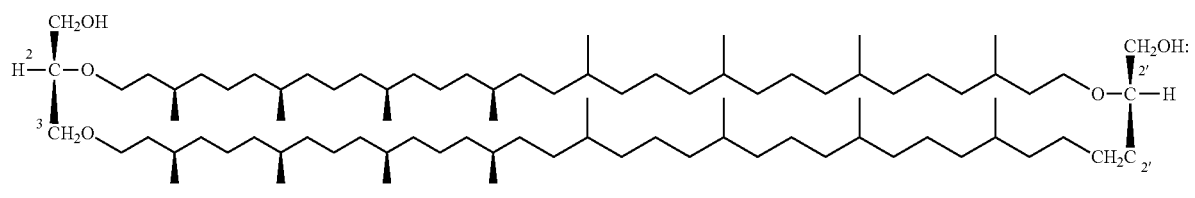
Isocalarcheol
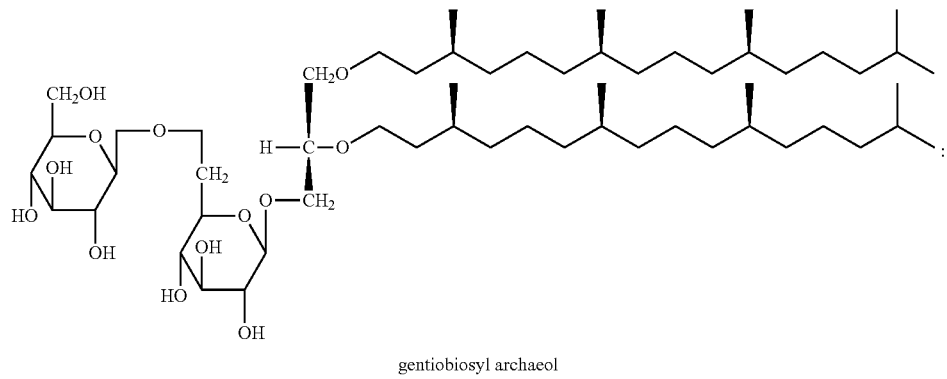
gentiobiosyl archaeol
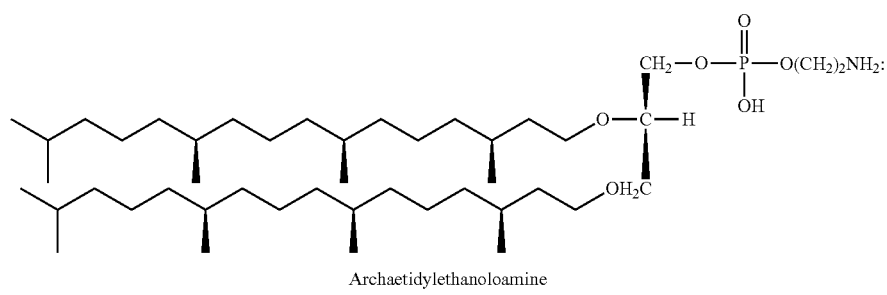
Archaetidylethanoloamine Gentyobiosyl caldarc haetidylethanoloamine The nanodisc may comprise any suitable shape, including a substantially round shape, an ovular or elliptical shape, a polygonal shape, or irregular shape. The nanodisc bilayer may comprise any suitable dimensions. The nanodisc bilayer may have a height of from about 1 nm to about 15 nm, preferably from about 1 nm to about 6 nm, from about 1 nm to about 5 nm, from about 2 nm to about 8 nm, from about 2 nm to about 6 nm, from about 3 nm to about 7 nm, from about 4 nm to about 6 nm, from about 4 nm to about 8 nm, from about 5 nm to about 10 nm, from about 5 nm to about 8 nm, from about 5 nm to about 7 nm, from about 6 nm to about 8 nm, from about 7 nm to about 10 nm, or from about 8 nm to about 10 nm though the nanodisc bilayer may have a height dimension greater than about 10 nm. The nanodisc bilayer may have a diameter, length, or width of from about 1 nm to about 20 nm, preferably from about 5 nm to about 15 nm, from about 5 nm to about 10 nm, from about 6 nm to about 12 nm, from about 6 nm to about 10 nm, from about 7 nm to about 15 nm, from about 7 nm to about 14 nm, from about 7 nm to about 13 nm, from about 7 nm to about 12 nm, from about 7 nm to about 11 nm, from about 7 nm to about 10 nm, from about 8 nm to about 15 nm, from about 8 nm to about 14 nm, from about 8 nm to about 13 nm, from about 8 nm to about 12 nm, from about 8 nm to about 11 nm, from about 8 nm to about 10 nm, about 9 nm to about 15 nm, from about 9 nm to about 14 nm, from about 9 nm to about 13 nm, from about 9 nm to about 12 nm, from about 9 nm to about 11 nm, or from about 10 nm to about 15 nm.

Figure 1:
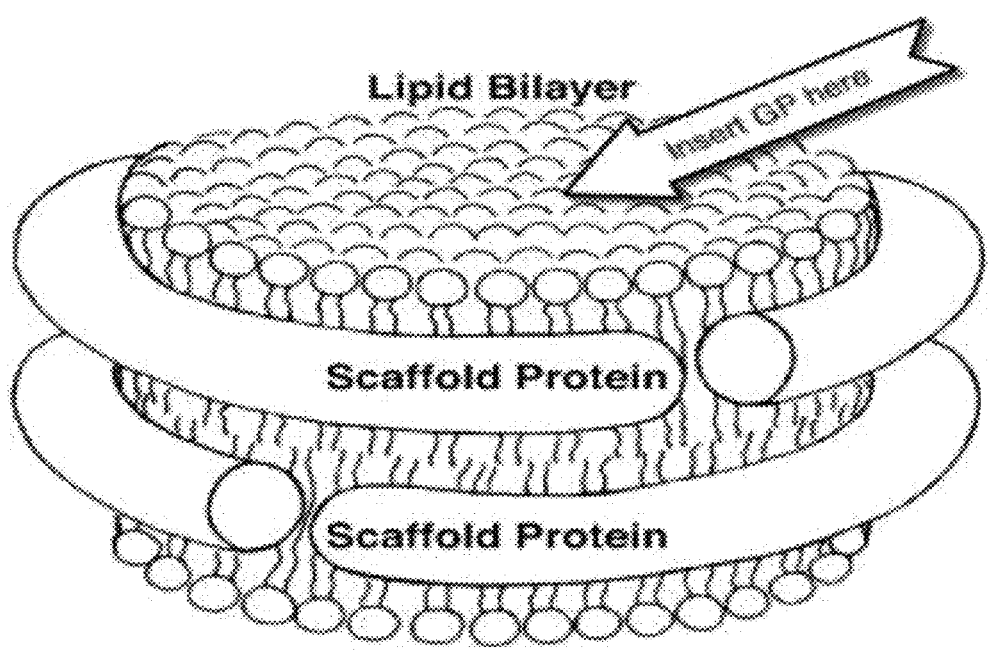
FIG. 1 shows a schematic drawing of a nanodisc. Two scaffold proteins are wrapped around a lipid bilayer in a belt-like fashion. The nanodisc structure is a non-covalent assembly of phospholipid and a genetically engineered "membrane scaffold protein" (MSP) based upon the sequence of human serum apolipoprotein A1.

The structural integrity of the nanodisc, as well as the compatibility of the nanodisc with an aqueous environment (the edges of the nanodisc will comprise a hydrophobic character, particularly near the center, owing to the hydrophobic hydrocarbon tails) is mediated, in part, by the inclusion of membrane scaffold proteins (MSPs), which wrap around the perimeter of the nanodisc, akin to a belt (FIG. 1). The MSPs may wrap multiple times around the perimeter of the nanodisc (FIG. 1). Given the hydrophobic character of the central regions of the outer perimeter of the nanodisc, it is preferred that the MSP comprise an amphipathic character, with at least one face of the secondary, tertiary, or quaternary structure of the MSP having a hydrophobic character (e.g., being substantially hydrophobic), and at least one face of the secondary, tertiary, or quaternary structure of the MSP having a hydrophilic character (e.g., being substantially hydrophilic). The hydrophobic face of the MSP would interface with the hydrophobic regions of the outer perimeter of the nanodisc, and the hydrophilic face of the MSP would point toward the external environment of the nanodisc, which is expected to be aqueous in nature (e.g., aqueous pharmaceutically acceptable carrier, and/or blood).

The MSP may comprise human apolipoprotein A1, or may comprise a fragment (e.g., peptide fragment) of human apolipoprotein A1. Human apolipoprotein A1 may comprise the amino acid sequence of SEQ ID NO:14. The MSP may comprise a variant (e.g., comprise one or more amino acid substitutions, deletions, or insertions) of human apolipoprotein A1 or fragment (e.g., peptide fragment) thereof. The MSP may comprise SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13, or may comprise a fusion of one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13. Such a fusion may be direct (e.g., N-terminal to C-terminal linkage) or indirect (e.g., via a synthetic linker such as a Gly-Ser linker peptide).

The nanodisc preferably comprises a vaccine antigen. The vaccine antigen may comprise a protein or a polypeptide, including a glycoprotein, lipoprotein, and other proteins that may elicit an immune response.

In some embodiments, the vaccine antigen comprises a microbial protein, preferably a viral protein, more preferably a microbial protein, and more preferably a viral envelope protein. In some embodiments, the vaccine antigen comprises an envelope protein from a DNA virus. In some embodiments, the vaccine antigen comprises an envelope from an RNA virus.

DNA viruses having envelope proteins suitable for use in the nanodisc carrier include the herpesvirus, poxvirus, and hepadnavirus. RNA viruses having envelope proteins suitable for use in the nanodisc carrier include togavirus, coronavirus, orthomyxovirus, paramyxovirus, rhabdovirus, bunyavirus, filovirus, and flavivirus. In some embodiments, the orthomyxovirus is an Influenza virus, including an influenza type A virus, influenza type B virus, and influenza type C virus. In some embodiments, the filovirus is the Ebola virus. In some embodiments, the flavivirus is the Zika virus.

In some embodiments, the virus envelope protein comprises the Influenza virus hemagglutinin protein. The hemagglutinin protein may comprise the amino acid sequence of SEQ ID NO:18. In some embodiments, the virus envelope protein comprises the Ebola virus protein VP40 or the Ebola virus GP protein, or both the VP40 and GP protein may be included in the nanodisc carrier. The VP40 protein may comprise the amino acid sequence of SEQ ID NO:15. The GP protein may comprise the amino acid sequence of SEQ ID NO:16. In some embodiments, the virus envelope protein comprises the Zika virus envelope protein. The Zika virus envelope protein may comprise the amino acid sequence of SEQ ID NO:17. Such viral envelope proteins may be recombinantly expressed, for example, via a virus-like nanoparticle (VLP) or via a nano-VLP, with the envelope protein purified, isolated, or otherwise obtained from the VLP or nano-VLP.

The viral envelope protein is preferably embedded in the nanodisc. The viral envelope protein is preferably embedded in the ether glycerophospholipid bilayer, for example, on either or both the top or bottom leaflet of the bilayer. For example, a hydrophobic portion of the envelope protein may be embedded within the hydrophobic center area of the bilayer (among the hydrophobic tails). It is preferred that the envelope protein is embedded in the bilayer in substantially the envelope protein's native conformation and that the protein is not substantially denatured. The protein also substantially retains its native conformation once embedded in the bilayer, as well as during storage of the nanodisc. Thus, the loading process does not substantially denature the viral envelope protein (e.g., exposure to detergents and/or high temperatures and/or detergent removing reagents during nanodisc preparation and self-assembly does not substantially denature the viral envelope protein (or the MSP)).

More than one viral envelope protein may be embedded in the nanodisc carrier. Thus, the vaccine may comprise multiple viral envelope proteins, and may comprise multiple different viral envelope proteins (e.g., for an Ebola virus vaccine, both the GP protein and the VP40 protein may be embedded in the nanodisc carrier).

The nanodiscs, including the viral envelope protein embedded therein, may be included in a composition comprising the nanodisc and a carrier, as well as one or more excipients, an adjuvant, or one or more excipients and an adjuvant (as the nanodiscs may have adjuvant qualities, the composition may comprise a separate adjuvant). The carrier is preferably a pharmaceutically acceptable carrier, preferably an aqueous carrier, and is preferably suitable for parenteral administration. Suitable carriers include any media that does not interfere with the antigenic character of the viral envelope protein and does not interfere with the capacity of the nanodisc+envelope protein to elicit a protective immune response, and preferably is not toxic to the subject to which it is administered. The carrier may comprise water, saline, or an aqueous alcohol, or a physiologically compatible buffer, such as Hanks's solution, Ringer's solution, or physiological saline buffer. The carrier may contain formulatory agents, such as suspending, stabilizing and/or dispersing agents. The carrier may also include a buffer or a pH adjusting agent. The buffer may be a salt prepared from an organic acid or base. Representative buffers include organic acid salts, such as salts of citric acid, ascorbic acid, gluconic acid, carbonic acid, tartaric acid, succinic acid, acetic acid, or phthalic acid, Tris, tromethamine hydrochloride, or a phosphate buffer. Preparations for parenteral administration include sterile solutions ready for injection, and sterile dry nanodiscs ready to be combined with a carrier just prior to use.

Nanodiscs as described and as exemplified herein, including the viral envelope protein embedded therein, may be used as vaccines, and administered to a subject in an amount effective to elicit a protective immune response against the viral envelope protein antigen that further protects the subject from infection by the virus from which the viral envelope protein is a part. The nanodiscs may be administered to the subject as a composition comprising a carrier, excipient, and/or adjuvant. Thus, the present disclosure provides methods for vaccinating a subject in need thereof.

In some embodiments, methods for vaccinating a subject in need thereof comprise administering to the subject an effective amount of any nanodisc comprising any microbial protein or viral envelope protein described or exemplified herein. The effective amount may comprise any amount sufficient to elicit a protective immune response that protects the subject from infection by the virus from which the microbial protein or viral envelope protein is a part. The nanodisc may be comprised in a composition comprising a carrier, excipient, and/or adjuvant. The nanodisc, or composition thereof, is preferably administered parenterally, which may comprise a subdermal, subcutaneous, intramuscular, intravenous, or intra-arterial injection. The administering step may be repeated any number of times (e.g., repeat once, twice, three, four, or more times) sufficient to confer or maintain protective immunity (e.g., boostering). Repeat administration may follow any suitable period of time, for example, a month, two months, three months, six months, twelve months, eighteen months, twenty four months, or longer periods (e.g., several years).

The present disclosure also provides kits. The kits comprise any nanodisc comprising any microbial protein or viral envelope protein described or exemplified herein, or composition thereof, and instructions for using the nanodisc or composition thereof in a method for vaccinating a subject in need thereof. The kits may further comprise a carrier or diluent for mixing together with the nanodiscs prior to administration. The kits may further comprise a container housing the nanodisc or composition thereof, for example, a syringe, vial, or diluent bag, and may further comprise a needle or catheter for administering the nanodisc or composition thereof to a subject.

Any nanodisc comprising any microbial protein or viral envelope protein described or exemplified herein may be for use in the manufacture of a medicament or a vaccine in the treatment or prevention of a viral infection. The nanodiscs comprising a viral envelope protein may be for use in the treatment or prevention of a herpesvirus infection. The nanodiscs comprising a viral envelope protein may be for use in the treatment or prevention of a poxvirus infection. The nanodiscs comprising a viral envelope protein may be for use in the treatment or prevention of a hepadnavirus infection. The nanodiscs comprising a viral envelope protein may be for use in the treatment or prevention of a togavirus infection. The nanodiscs comprising a viral envelope protein may be for use in the treatment or prevention of a coronavirus infection. The nanodiscs comprising a viral envelope protein may be for use in the treatment or prevention of a orthomyxovirus infection. The nanodiscs comprising a viral envelope protein may be for use in the treatment or prevention of a paramyxovirus infection. The nanodiscs comprising a viral envelope protein may be for use in the treatment or prevention of a rhabdovirus infection. The nanodiscs comprising a viral envelope protein may be for use in the treatment or prevention of a bunyavirus infection. The nanodiscs comprising a viral envelope protein may be for use in the treatment or prevention of a filovirus infection. The nanodiscs comprising a viral envelope protein may be for use in the treatment or prevention of a flavivirus infection. The nanodiscs comprising a viral envelope protein may be for use in the treatment or prevention of an influenza type A virus infection. The nanodiscs comprising a viral envelope protein may be for use in the treatment or prevention of an influenza type B virus infection. The nanodiscs comprising a viral envelope protein may be for use in the treatment or prevention of an influenza type C virus infection. The nanodiscs comprising a viral envelope protein may be for use in the treatment or prevention of an Ebola virus infection. The nanodiscs comprising a viral envelope protein may be for use in the treatment or prevention of a Zika virus infection.

The present disclosure also provides methods for preparing thermostable nanodisc vaccines. In general, the methods comprise mixing one or more membrane scaffold proteins (MSP), one or more microbial proteins e.g., one or more viral envelope proteins, and one or more ether glycerophospholipids together in an aqueous media comprising a detergent, removing the detergent and allowing the one or more membrane scaffold proteins and the one or more ether glycerophospholipids to self-assemble into a thermostable nanodisc comprising the one or more microbial proteins e.g., one or more viral envelope proteins, embedded therein, thereby forming a thermostable nanodisc vaccine. The one or more membrane scaffold proteins may comprise any membrane scaffold protein described or exemplified herein, the one or more ether glycerophospholipids may comprise any ether glycerophospholipid described or exemplified herein, and the microbial protein may comprise any microbial protein described or exemplified herein, including any viral envelope protein described or exemplified herein. Optionally, the thermostable nanodisc vaccine may be dried or lyophilized, then later reconstituted, for example, as a composition comprising a pharmaceutically acceptable carrier and/or excipient and/or adjuvant for administration as part of a vaccine regimen. In the nanodisc prepared according to the method, the microbial protein substantially retains its native conformation, as the protein is not substantially denatured during the mixing, detergent removal, or self-assembly steps.

During the step of mixing one or more membrane scaffold proteins (MSP), one or more microbial proteins e.g., one or more viral envelope proteins, and one or more ether glycerophospholipids together, the ratio of phospholipids to MSP may be from about 20:1 to about 200:1 (phospholipids: MSP), including from about 20:1 to about 180:1, from about 20:1 to about 150:1, from about 20:1 to about 100:1, from about 20:1 to about 80:1, from about 20:1 to about 50:1, from about 20:1 to about 40:1, from about 40:1 to about 200:1, from about 40:1 to about 160:1, from about 40:1 to about 140:1, from about 40:1 to about 120:1, from about 40:1 to about 100:1, from about 40:1 to about 80:1, from about 40:1 to about 60:1, from about 50:1 to about 200:1, from about 50:1 to about 150:1, from about 50:1 to about 100:1, from about 50:1 to about 75:1, from about 60:1 to about 200:1, from about 60:1 to about 180:1, from about 60:1 to about 120:1, from about 60:1 to about 90:1, from about 80:1 to about 200:1, from about 80:1 to about 190:1, from about 80:1 to about 180:1, from about 80:1 to about 160:1, from about 80:1 to about 120:1, from about 80:1 to about 100:1, from about 100:1 to about 200:1, from about 100:1 to about 150:1, from about 100:1 to about 125:1, from about 100:1 to about 120:1, from about 120:1 to about 200:1, from about 120:1 to about 180:1, from about 120:1 to about 160:1, from about 125:1 to about 150:1, from about 140:1 to about 180:1, from about 140:1 to about 160:1, from about 150:1 to about 200:1, or from about 180:1 to about 200:1. The ratio may vary, for example, based on the phospholipid used, the MSP used, or both the phospholipid and MSP used.

The ratio of microbial protein antigen (e.g., viral envelope protein) to MSP may be from about 1:2 to about 1:20 (antigen:MSP), from about 1:2 to about 1:18, from about 1:2 to about 1:16, from about 1:2 to about 1:14, from about 1:2 to about 1:12, from about 1:2 to about 1:10, from about 1:2 to about 1:8, from about 1:2 to about 1:6, from about 1:2 to about 1:4, from about 1:3 to about 1:18, from about 1:3 to about 1:15, from about 1:3 to about 1:12, from about 1:3 to about 1:9, from about 1:3 to about 1:6, from about 1:4 to about 1:16, from about 1:4 to about 1:12, from about 1:4 to about 1:8, from about 1:5 to about 1:20, from about 1:5 to about 1:15, from about 1:5 to about 1:10, from about 1:6 to about 1:17, from about 1:6 to about 1:11, from about 1:8 to about 1:18, from about 1:8 to about 1:16, from about 1:8 to about 1:12, from about 1:10 to about 1:20, from about 1:10 to about 1:15, from about 1:10 to about 1:12, from about 1:12 to about 1:16, from about 1:12 to about 1:14, from about 1:13 to about 1:16, from about 1:13 to about 1:15, from about 1:15 to about 1:20, from about 1:15 to about 1:18, from about 1:16 to about 1:20, or from about 1:16 to about 1:18.

Nanodisc assembly temperature may depend, for example, on the particular lipid. The temperature may range from about 4 degrees C. to about 50 degrees C., from about 25 degree C. to about 50 degrees C., from about 25 degree C. to about 37 degrees C., from about 25 degrees C. to about 40 degrees C., from about 37 degrees C. to about 50 degrees C., or from about 37 degrees C. to about 45 degrees C. Assembly may be carried out at about 25 degrees C., at about 37 degrees C., at about 40 degrees C., at about 45 degrees C., or at about 50 degrees C.

For removing the detergent, the ratio of detergent-removing beads (e.g., AMBERLITE® beads) to detergent can be from about 10:1 to 100:1, from about 20:1 to about 90:1, from about 20:1 to about 80:1, from about 20:1 to about 60:1, from about 30:1 to about 90:1, from about 30:1 to about 80:1, from about 30:1 to about 70:1, or from about 25:1 to about 85:1.

The expression and ensuing oligomerization of the Ebola matrix protein VP40 is the only viral element required to drive formation of filamentous, enveloped VLPs that are subsequently discharged from cells. The efficiency of production of VLPs driven by the sole expression of VP40, however, is poor. VLP formation and release are dramatically increased by the presence of the GP envelope protein. The membrane-bound form of GP is believed to enhance VP40 VLP release.

Figure 3:
FIG. 3 shows a schematic of the gene cassette for STEP® technology.

Since expression of the GP protein adversely affects cells by a phenomenon termed GP-mediated cytopathology, the STEP® (Batavia Biosciences BV) platform technology may be used to construct a stable cell line that expresses VP40 alone (FIG. 3). To select clones with optimal integration of the VP40 gene, GP-containing VLPs induced by subsequent transfection with GP DNA were used as the selection method to identify the most appropriate clone to use for subsequent production of VLPs.

Figure 2:
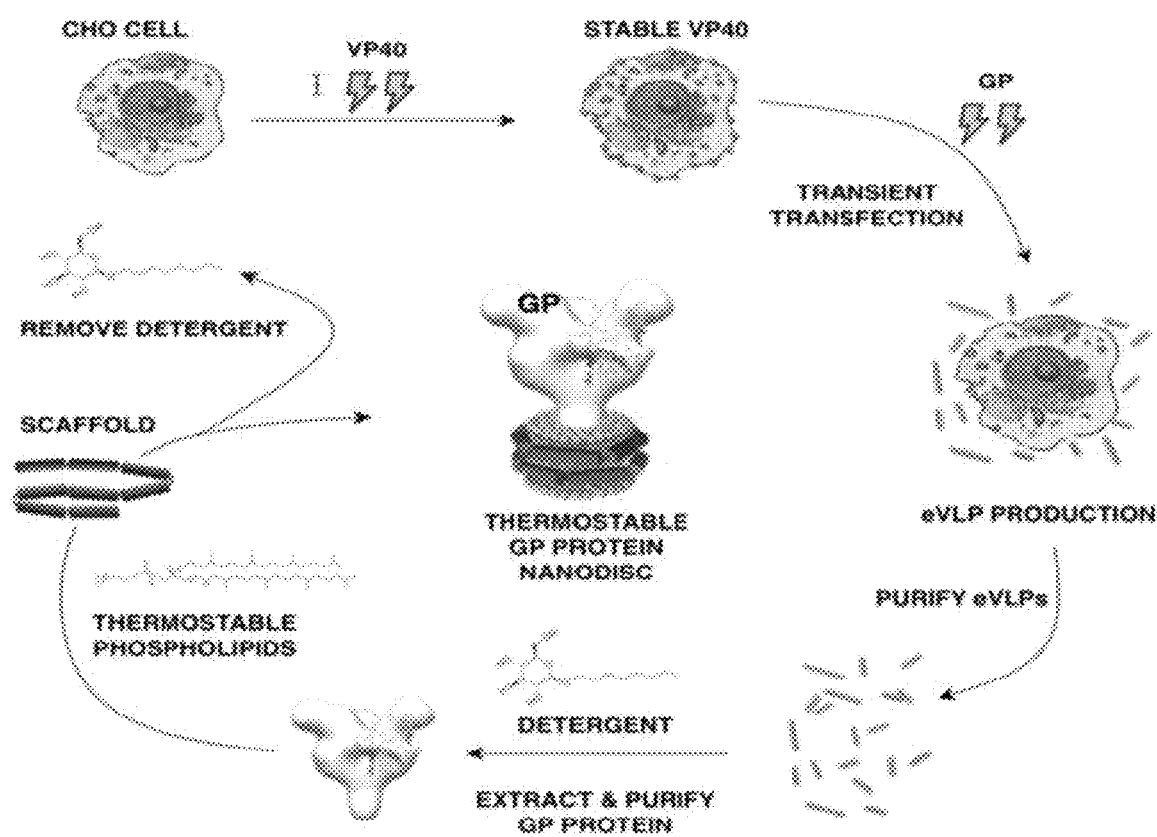
FIG. 2 shows a schematic overview of the processes that are employed to manufacture a thermostable nanodisc-based vaccine directed against Zaire Ebola viral GP protein. The structure shown for the detergent is octylglucoside, while an isoprene-based glycoether phospholipid is shown to represent lipids found in the thermostable membranes of archaebacteria. The actual detergents and lipids used may differ from these structures.

Once the stable cell line is identified, a MAXCYTE STX® (MaxCyte, Inc.) high cell mass electroporation instrument (flow electroporation) is used to transiently transfect the VP40 expressing cells (e.g., CHO cells or HEK 293 cells) with GP DNA, thereby inducing the cells to produce high quantities of Ebola VLPs containing the GP antigen. The resultant VLPs are separated away from cells and other debris, and then, full-length GP antigen is purified from the VLPs. Purified GP protein may then be loaded/incorporated into the thermostable nanodiscs (e.g., those comprising ether glycerophospholipids for enhanced thermostability). An overview is presented in schematic form in FIG. 2. Initially, experiments are performed to optimize the electroporation process, ascertaining the optimal amount of DNA required to maximize VLP productivity. Following a recovery period, the cells are suspended in media supplemented with lipids to facilitate the continual budding and discharge of GP-studded VLPs.

In some embodiments, Ebola VLPs are removed from the CHO or HEK 293 cells by filtration, and concentrated, for example, with tangential flow filtration. The highly pleiotropic distribution of particle sizes may be reduced to smaller size by sonication or micro fluidization (e.g., producing nano-VLPs), filtered through a glass-fiber filter, and then further purified through a cation exchange membrane filter (Sartorius) and a CAPTO® Core 700 column (GE HealthCare) to remove nucleic acids and residual host cell contaminants. The particles may be subjected to additional sonication or micro fluidization to reduce their overall size to a minimum, and then filtered through a 0.45 micron filter to reduce bio burden.

The purified VLPs may be extracted with a detergents, using both SDS-PAGE and ELISA analysis (e.g., using conformationally-sensitive monoclonal antibodies 13C6 and 6D3) so as to establish the best differential solubilization possible (e.g., identify the detergent that yields the highest recovery of conformationally-recognizable GP protein in highest relative quantity compared to all other VLP components). GP solubilized with detergent is further purified away from any other contaminants, with a major emphasis on exploiting its very large mass (~600 kD) to achieve the separation. Chromatography on size-exclusion mixed chromatography resins (CAPTO® Core 700 and equivalent type resins) and entirely size-dependent size exclusion chromatography (SEC) exploit this feature of the protein in order to purify it away from contaminants. GP is very highly glycosylated (carbohydrates compose nearly half its mass) and lectin affinity chromatography may also be useful to enhance its purity as well. Additionally, once GP is solubilized with detergent, nanofiltration may be performed employing membranes with pores sufficiently small to exclude any viruses and virus-like particles, whether endogenous ones budded from the cells or others adventitious in nature. It is desirable to achieve a high degree of purity, taking care to incorporate steps intended to reduce contamination with undesirable contaminants such as nucleic acids and host cell proteins.

Once purified, the GP protein can be mixed with a membrane scaffold protein (MSP) and thermostable lipids (e.g., ether glycerophospholipids), including those analogous to the lipids found in archaebacteria as well as those semi-synthetically produced. Self-assembly of nanodiscs is initiated by the removal of detergent, and nanodiscs containing embedded single copies of trimeric GP are isolated from nanodiscs lacking GP protein by straightforward SEC using a SUPERDEX® column (GE Healthcare Bio-Sciences A.B.). The GP-containing nanodiscs can be aliquoted into various quantities in vials and lyophilized for storage. The final lyophilized product may be subsequently evaluated for thermostability and immunogenicity.

The procedures described above for GP protein may also be used in the preparation of nanodisc-based vaccines against other virus envelope antigens (e.g., HIV Env and influenza virus hemagglutinin (HA)). Furthermore, if the thermostable ether glycerophospholipids retain an adjuvant character similar to the adjuvant character observed for archaebacterial lipids, the potency of the resultant vaccines may enable transfection with not only a single DNA sequence, but many sequences coding for variants of the corresponding envelope antigen. For Ebola, this would mean transfecting not only with the sequence of the GP protein found in Zaire, but also with the sequences of GP present in the other four known strains, and/or with any new emergent infectious strain or variant. A similar strategy is followed for other enveloped viruses possessing antigens with extensive variability or drift in the viral strains encountered in the field.

The present disclosure also provides processes for producing Ebola GP protein, comprising transfecting an Ebola VP40 protein-producing stable CHO cell with a gene encoding the Ebola GP protein, isolating VLPs comprising Ebola VP40 protein and Ebola GP protein produced from the transfected CHO cell, separating the GP protein from the VP40 protein, and purifying the separated GP protein.

VLPs are used as a highly enriched source from which viral envelope protein antigens can be purified following their extraction and solubilization with detergent. Once purified to biopharmaceutical standards, the envelope protein can be loaded into a thermostable nanodisc carrier in a way that resembles or mimics the natural environment or habitat that the envelope protein experiences in the virion.

The present disclosure also provides CHO or HEK 293 cells stably transformed with a gene encoding the Ebola virus VP40 protein, or with a gene encoding the Ebola virus GP protein, or with a gene encoding the Ebola virus VP40 protein and the Ebola virus GP protein, which cells express the VP40 protein, or express the GP protein, or express both the VP40 protein and the GP protein. Such cells, and methods for producing them, are provided.

The following representative embodiments are presented:

Embodiment 1

A thermostable vaccine carrier, comprising a bilayer comprising one or more ether glycerophospholipids and one or more membrane scaffold proteins self-assembled into a nanodisc, and a microbial protein antigen embedded into the nanodisc.

Embodiment 2

The thermostable vaccine carrier according to embodiment 1, wherein the one or more ether glycerophospholipids is selected from the group consisting of 1,2-di-O-phytanyl-sn-glycero-3-phosphocholine, 1,2-di-O-phytanyl-sn-glycero-3-phosphoethanolamine, glycerol dialkyl glycerol tetraether, 1,2-di-O-octadecyl-sn-glycero-3-phosphocholine, 1,2-di-O-(9Z-octadecenyl)-sn-glycero-3-phosphocholine, 2-3-diphytanyl-O-sn-glycerol (archaeol), caldarcheol, isocalarcheol, gentiobiosyl archaeol, archaetidylethanoloamine, gentyobiosyl caldarc haetidylethanoloamine, and combinations thereof.

Embodiment 3

The thermostable vaccine carrier according to embodiment 1 or 2, wherein the one or more ether glycerophospholipids comprises 1,2-di-O-phytanyl-sn-glycero-3-phosphocholine.

Embodiment 4

The thermostable vaccine carrier according to embodiment 1 or 2, wherein the one or more ether glycerophospholipids comprises 1,2-di-O-phytanyl-sn-glycero-3-phosphoethanolamine.

Embodiment 5

The thermostable vaccine carrier according to embodiment 1 or 2, wherein the one or more ether glycerophospholipids comprises glycerol dialkyl glycerol tetraether.

Embodiment 6

The thermostable vaccine carrier according to any one of embodiments 1 to 5, wherein the membrane scaffold protein comprises a human apolipoprotein A1 fragment peptide or a variant thereof having one amino acid substitution or deletion.

Embodiment 7

The thermostable vaccine carrier according to any one of embodiments 1 to 6, wherein the membrane scaffold protein has the amino acid sequence of SEQ ID NO:1.

Embodiment 8

The thermostable vaccine carrier according to any one of embodiments 1 to 6, wherein the human apolipoprotein A1 fragment peptide has an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13.

Embodiment 9

The thermostable vaccine carrier according to any one of embodiments 1 to 8, wherein the microbial protein antigen is a virus envelope protein.

Embodiment 10

The thermostable vaccine carrier according to any one of embodiments 1 to 8, wherein the microbial protein antigen is a virus envelope protein, and the virus is a DNA virus.

Embodiment 11

The thermostable vaccine carrier according to embodiment 10, wherein the DNA virus is a herpesvirus.

Embodiment 12

The thermostable vaccine carrier according to embodiment 10, wherein the DNA virus is a poxsvirus.

Embodiment 13

The thermostable vaccine carrier according to embodiment 10, wherein the DNA virus is a hepadnavirus.

Embodiment 14

The thermostable vaccine carrier according to any one of embodiments 1 to 8, wherein the microbial protein antigen is a virus envelope protein, and the virus is an RNA virus.

Embodiment 15

The thermostable vaccine carrier according to embodiment 14, wherein the RNA virus is a togavirus.

Embodiment 16

The thermostable vaccine carrier according to embodiment 14, wherein the RNA virus is a coronavirus.

Embodiment 17

The thermostable vaccine carrier according to embodiment 14, wherein the RNA virus is an orthomyxovirus.

Embodiment 18

The thermostable vaccine carrier according to embodiment 17, wherein the orthomyxovirus is an Influenza virus.

Embodiment 19

The thermostable vaccine carrier according to embodiment 18, wherein the Influenza virus envelope protein is hemagglutinin and comprises the amino acid sequence of SEQ ID NO:18.

Embodiment 20

The thermostable vaccine carrier according to embodiment 14, wherein the RNA virus is a paramyxovirus.

Embodiment 21

The thermostable vaccine carrier according to embodiment 14, wherein the RNA virus is a rhabdovirus.

Embodiment 22

The thermostable vaccine carrier according to embodiment 14, wherein the RNA virus is a bunyavirus.

Embodiment 23

The thermostable vaccine carrier according to embodiment 14, wherein the RNA virus is a filovirus.

Embodiment 24

The thermostable vaccine carrier according to embodiment 23, wherein the filovirus is Ebola virus.

Embodiment 25

The thermostable vaccine carrier according to embodiment 24, wherein the Ebola virus envelope protein is VP40 and comprises the amino acid sequence of SEQ ID NO:15.

Embodiment 26

The thermostable vaccine carrier according to embodiment 24, wherein the Ebola virus envelope protein is GP and comprises the amino acid sequence of SEQ ID NO:16.

Embodiment 27

The thermostable vaccine carrier according to embodiment 14, wherein the RNA virus is a flavivirus.

Embodiment 28

The thermostable vaccine carrier according to embodiment 27, wherein the flavivirus is Zika virus.

Embodiment 29

The thermostable vaccine carrier according to embodiment 28, wherein the Zika virus envelope protein comprises the amino acid sequence of SEQ ID NO:17.

Embodiment 30

A composition, comprising the thermostable vaccine carrier according to any one of embodiments 1 to 29 and a pharmaceutically acceptable carrier.

Embodiment 31

The composition according to embodiment 30, further comprising a pharmaceutically acceptable excipient.

Embodiment 32

The composition according to embodiment 30 or 31, further comprising an adjuvant.

Embodiment 33

A kit, comprising the thermostable vaccine carrier according to any one of embodiments 1 to 26, a container containing the carrier, and instructions for using the carrier in a method for vaccinating a subject in need thereof.

Embodiment 34

The kit according to embodiment 33, wherein the thermostable vaccine carrier is comprised in a composition comprising a pharmaceutically acceptable carrier and optionally a pharmaceutically acceptable excipient, an adjuvant, or a pharmaceutically acceptable excipient and an adjuvant.

Embodiment 35

The kit according to embodiment 33 or 34, wherein the container comprises a syringe or diluent bag, and further comprising a needle or catheter for administering the thermostable vaccine carrier or composition to a subject in need thereof.

Embodiment 36

A method for vaccinating a subject in need thereof, comprising administering to the subject the thermostable vaccine carrier according to any one of embodiments 1 to 29 in an amount effective to confer an immune response against the microbial protein antigen in the subject.

Embodiment 37

The method according to embodiment 36, wherein the thermostable vaccine carrier is comprised in a composition comprising a pharmaceutically acceptable carrier and optionally a pharmaceutically acceptable excipient, an adjuvant, or a pharmaceutically acceptable excipient and an adjuvant.

Embodiment 38

The method according to embodiment 36 or 37, wherein the administering comprises injecting the thermostable vaccine carrier or composition subcutaneously, intramuscularly, or intravenously in the subject.

Embodiment 39

Use of the thermostable vaccine carrier according to any one of embodiments 1 to 29 in the manufacture of a medicament or a vaccine.

Embodiment 40

Use of the thermostable vaccine carrier according to any one of embodiments 1 to 29 in the treatment or prevention of a virus infection.

Embodiment 41

Use of the thermostable vaccine carrier according to embodiment 11 in the treatment or prevention of a herpesvirus infection.

Embodiment 42

Use of the thermostable vaccine carrier according to embodiments 12 in the treatment or prevention of a poxsvirus infection.

Embodiment 43

Use of the thermostable vaccine carrier according to embodiment 13 in the treatment or prevention of a hepadnavirus infection.

Embodiment 44

Use of the thermostable vaccine carrier according to embodiment 15 in the treatment or prevention of a togavirus infection.

Embodiment 45

Use of the thermostable vaccine carrier according to embodiment 16 in the treatment or prevention of a coronavirus infection.

Embodiment 46

Use of the thermostable vaccine carrier according to embodiment 17 in the treatment or prevention of an orthomyxovirus infection.

Embodiment 47

Use of the thermostable vaccine carrier according to embodiment 18 or embodiment 19 in the treatment or prevention of an Influenza virus infection.

Embodiment 48

Use of the thermostable vaccine carrier according to embodiment 20 in the treatment or prevention of a paramyxovirus infection.

Embodiment 49

Use of the thermostable vaccine carrier according to embodiment 21 in the treatment or prevention of a rhabdovirus infection.

Embodiment 50

Use of the thermostable vaccine carrier according to embodiment 22 in the treatment or prevention of a bunyavirus infection.

Embodiment 51

Use of the thermostable vaccine carrier according to embodiment 23 in the treatment or prevention of a filovirus infection.

Embodiment 52

Use of the thermostable vaccine carrier according to anyone of embodiments 24 to 26 in the treatment or prevention of an Ebola virus infection.

Embodiment 53

Use of the thermostable vaccine carrier according to embodiment 27 in the treatment or prevention of a flavivirus infection.

Embodiment 54

Use of the thermostable vaccine carrier according to embodiment 28 in the treatment or prevention of a Zika virus infection.

Embodiment 55

A method for making thermostable vaccine carrier according to any one of embodiments 1 to 29, comprising mixing the one or more ether glycerophospholipids, the one or more membrane scaffold proteins, and the microbial protein antigen in an aqueous media comprising a detergent, removing the detergent, and allowing the one or more membrane scaffold proteins and the one or more ether glycerophospholipids to self-assemble into the nanodisc having the microbial protein antigen embedded therein.

Embodiment 56

The method according to embodiment 55, further comprising lyophilizing the nanodisc.

Embodiment 57

A process for producing substantially pure Ebola GP protein, comprising transfecting Ebola VP40 protein-expressing stable cells with a gene encoding the Ebola GP protein, isolating virus-like particles comprising the Ebola VP40 protein and Ebola GP protein produced from the transfected cells, separating the GP protein from the VP40 protein, and purifying the separated GP protein.

Embodiment 58

The process according to embodiment 57, wherein the stable cells are Chinese Hamster Ovary (CHO) cells.

Embodiment 59

Mammalian cells stably transformed with a recombinant gene encoding the Ebola virus VP40 protein.

Embodiment 60

The mammalian cells according to embodiment 59, further transformed with a recombinant gene encoding the Ebola virus GP protein.

Embodiment 61

The mammalian cells according to embodiment 59 or 60, wherein the cells are Chinese Hamster Ovary (CHO) cells or Human Embryonic Kidney 293 (HEK 293) cells.

The following examples are provided to describe the subject matter in greater detail. They are intended to illustrate, not to limit, the claimed subject matter.

Example 1: Optimization of High Cell-Mass, Electroporation-Based Transfection Methods to Produce eVLPs from Mammalian Cell Lines Since Ebola VLPs are a source from which the antigenic component of the vaccine (GP) is prepared, it is desirable to develop a robust approach to produce such VLPs in sufficient quantities. While there are many reports of Ebola VLPs being prepared by transient transfection of HEK293 cells, the approach has been described as complicated by inefficient and poorly reproducible transfection results and low yields. It is believed that this may be explained, at least in part, by the phenomenon termed GP-mediated cytopathology, as well as the difficulty of expanding cells post-transfusion due to the high burden placed upon them by the continual efflux of eVLPs budding from their cell membrane.

Recent improvements in flow electroporation methodology have enabled the transient transfection of very high-density cell cultures, ranging up to $1\times10^{11}$ cells. The technology involves the application of an electric field to a cell suspension, causing the membranes of the cells to become transiently permeable, encouraging exogenous DNA to enter the cell. Optimization of the technique has led to the routine achievement of loading efficiencies exceeding 90%, and provided an avenue to successfully transform cells where reproducibility, efficiency, and the need for increased cell numbers are important.

Flow electroporation significantly improves both the reliability and yield of VLPs. One drawback of this technology is the large quantities of purified DNA that the electroporation requires when used to transiently transfect high-density cell cultures. A second drawback is that to produce VLPs decorated with GP, the host cells must be coerced to express the matrix protein, VP40 as well as the envelope antigen, GP. This doubles the amount of DNA required, and now that two species of DNA are required, it necessitates careful optimization and control of both the ratio and quantities of DNA. While such a co-transfection approach is pursued to obtain material to develop purification processes for the VLPs and GP protein, a stable cell line was constructed, which solely expresses the VP40 matrix protein, thus requiring only transfection with a single DNA sequence encoding the full-length GP protein to produce VLPs decorated with GP.

USAMRID has supplied two plasmids encoding for VP40 and GP, which is amplified to produce sufficient plasmid DNA to enable experiments to optimize parameters for large-scale production of Ebola VP. Three small-scale transient transfections using OC-400 cassettes for optimizing various parameters are performed, followed by six large-scale transfections using CL-2 bags.

A. Co-Transfection Methodology

In the first small-scale experiment, the optimal ratios and quantities of DNA needed to attain maximal VLP productivity are determined. A total of twelve transfections are performed per cell line (CHO cells and HEK 293 cells); nine comprise varying the total amount of DNA employed (ranging from 200 to 400 micrograms) and their ratios (evaluating 2:1, 1:1, and 1:2). The remaining three transfections are control-related to ensure the absence of any issues with the performance of the equipment.

A second optimization experiment explores the feasibility of first transfecting with VP40 DNA, and then conducting a second transfection with GP DNA after the cells are allowed to recover for periods of 5, 24, or 48 hours. In this experiment whether secondary transfection with DNA encoding the viral nucleoprotein (NP) further enhances VLP productivity is explored.

In the third small-scale transfection whether overall VLP productivity can be enhanced by inclusion of lipid supplements to the media post-transfection is evaluated. The intent is to promote the general well-being and longevity of cells that are constantly burdened with budding and discharging VLPs from their membranes.

After determining optimal parameters, six larger-scale co-transfections are performed to supply material to jump-start development and refinement of processes to isolate and purify VLPs and the GP protein.

B. Stable VP40 Cell Line Construction

To accelerate the construction and development of a stable cell line expressing VP40, STEP® technology (Batavia Bioservices BV Corp., Netherlands) a rapid plasmid-based system for generating high expressing, protein producing, mammalian (CHO) cell lines, is employed. The detailed preparation and materials used in the STEP® technology provided in U.S. Publ. No. 2012/156672, U.S. Publ. No. 2013/157312, and U.S. Publ. No. 2013/-23695.

An efficient selection system creating stably transfected mammalian cell lines requires killing un-transfected cells and achieving high protein expression levels.

The STEP® plasmid contains a very efficient, yet flexible, stringent cell selection system. Due to the translation of functionally impaired selection marker proteins, STEP® procedures eliminate un-transfected cells and low-expressing cells. Only cells that have very high mRNA expression levels are able to survive selective pressure—eliminating low-expressing cell lines, therefore greatly reducing the number of cell lines that need to be screened.

The Gene of Interest (GOI), encoding the desired therapeutic protein, is inserted into the plasmid using standard DNA approaches. The functionally impaired Zeocin (FI-Zeo) selection marker and DNA spacer create the highly stringent selection system. Linkage of the FI-Zeo marker to GOI via an internal ribosomal entry site (IRES) sequence results in high GOI expression, one RNA. The novel expression-enhancing (EE) elements, flanking the gene of interest (GOI), increase gene expression and allow cells to survive under high stringency (see FIG. 3). These are necessary to produce any clones. Without the flanking enhancing elements, no clones would survive. A unique feature of STEP® technology is that once clones are selected under antibiotic selection, they have proven stable producers in the absence of antibiotic.

In the STEP® procedure, three different Zeocin selection protein mutants—noted as low, medium, and high stringency—are spliced into different cassettes to ensure success in any transfection. The lowest stringency plasmid produces the highest number of clones. The higher the stringency, fewer surviving clones are produced, but with potentially higher expression. However, when this strategy was successfully used to express difficult to produce proteins such as Factor VIII, high expressing clones were obtained only at the lowest stringency. There were no surviving clones at the medium or highest stringency. In the case of a less difficult protein, EPO, all three stringencies produced clones, but the highest levels of EPO were produced at the highest level of expression.

The VP40 gene is synthesized at a vendor of choice according to regulations intended to achieve TSE-risk reduction. The synthetic gene is cloned into three STEP® vectors with low, intermediate, and high stringencies, using materials without components of animal origin. Use of restriction endonucleases are performed and DNA gel electrophoresis according to in-house BBI protocols. After the final construction step is completed, the STEP® vectors are treated with chaotropic salts and transformed into animal-component-free competent *E. coli*. Colonies are picked and grown under TSE-free conditions, and DNA are extracted by midi prep and checked for both gene and element integrity by digestion analysis.

GMP CHO cells, in culture for 2-2.5 weeks after revival, are concentrated for the transfection to ~$1.3\times10^6$ vc/ml. A total of 1.5 ml of cells are centrifuged in 1.5 ml sterile tubes, thereby attaining ~$2\times10^6$ CHO cells per sample with 5 μg DNA. A total of 14 nucleofections are performed for pool generation following BBI protocols: 4× nucleofections: STEP®-VP40 (lowest stringency); 4× nucleofections: STEP®-VP40 (intermediate stringency); 4× nucleofections: STEP®-VP40 (highest stringency); 1× nucleofection of STEP® plasmid (lowest stringency) lacking GOI (Null Cell Line); and 1× nucleofection of cells only; the latter two are controls.

Following drug restriction, surviving pools are expanded and serially diluted into a total of twenty 96 well plates at 0.3 cells per well, or −30 cells per 96 well plate. A visual assessment of each well is conducted to ensure clonality. A total of 150 clones are expanded. If only the low stringency pools survive, than 150 clones from this level are continued. If all three stringencies produce pools, then 50 clones are continued from each level of stringency.

The 150 pools are expanded and transiently transfected in cuvettes with the GP-containing plasmid in groups of 24. On harvest day, the spent medium are centrifuged and or filtered to remove cells. Each clone is analyzed in triplicate by ELISA to determine the clones that produce the highest amount of GP-containing VLPs. The top 24 clones are expanded, cryopreserved and transiently transfected with GP DNA using MAXCYTE® cassettes (MaxCyte, Inc). Each clone is analyzed by ELISA to determine the highest titer in a larger scale transfection versus the cuvette. The highest expressing clone is expanded and transfected with GP DNA in CL-2 bags producing 4-5 liters of product. This is repeated a second time before executing the final transfection at twice the volume using GP DNA manufactured with very low endotoxin levels.

The selected clone is that stable clone which expresses VP40 matrix protein in such a fashion as to maximize VLP production upon introduction of GP DNA by flow electroporation transfection.

The construction of a stable VP40 cell line enables the production of VLPs decorated with whatever envelope protein is encoded by the DNA introduced in the transfection; modifying the DNA sequence to correspond to a new emergent strain or using a collection of very similar sequences to provide immunity against several closely related strains now becomes a straightforward option.

Example 2: Refinement and Scale-Up of a Process to Prepare and Purify eVLPs from CHO Cells Using VLPs produced by large-scale (5 liters), nano-VLPs are produced as described below. A dead-end filtration process is configured to replace the initial low-speed centrifugation to remove cells and debris while tangential flow filtration is used instead of high-speed centrifugation to concentrate the VLPs. These changes render the process more scalable and suitable for manufacturing.

Once concentrated, the VLPs are sonicated to convert them into smaller species, termed Nano-VLPs. The process of sonication also considerably reduces their size distribution. The Nano-VLPs are then filtered through a glass-fiber, capsule filter, and subsequently subjected to flow-through chromatography using a cation-exchange membrane device (Sartobind S), and a novel CAPTO® Core 700 (GE Healthcare) column to remove nucleic acids and other smaller contaminants. The Nano-VLPs are sonicated a second time and then the bio burden is reduced by filtration through a 0.45 micron filter.

Example 3: Purification of GP Viral Protein (Full-Length) from eVLPs

Figure 4:
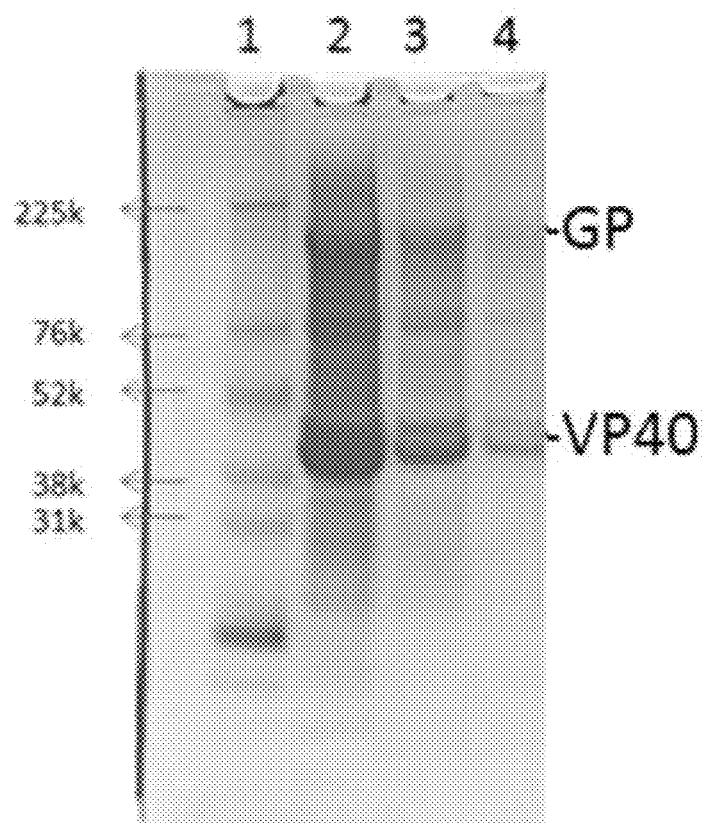
FIG. 4 shows a SDS-PAGE analysis of Nano-VLP preparation. Lane 1: MW marker (High Range Rainbow Marker, GE Lifesciences RN75E6). Lane 2: 15 μL of Nano-VLP. Lane 3: 5 μL of Nano-VLP. Lane 4: 2 μL of Nano-VLP. Samples were run under reduced conditions on a 4-12% Bis-Tris Gel (Invitrogen NP0321).

GP is a predominant component of the Nano-VLPs; only the highly oligomeric VP40 matrix protein is present in greater amounts (FIG. 4). This makes them an enriched source of GP protein, facilitating purification of this viral antigen for subsequent inclusion in the vaccine.

Once Nano-VLPs are highly purified, differential solubilization of the protein from most of the other components of the VLPs can be achieved using a number of non-ionic detergents, (e.g., dodecyl-maltoside or octyl-glucoside are two representative candidates).

Since native GP protein is a very large homotrimer; once it is solubilized into a monodisperse form with detergent, its Stokes radius or apparent size are in excess of 600 kD. This property can be effectively leveraged to purify the protein away using TABLE 1-continued Commercially Available Ether Phospholipids 1,2-di-O-phytanyl-sn-glycero-3-phosphoethanolamine:

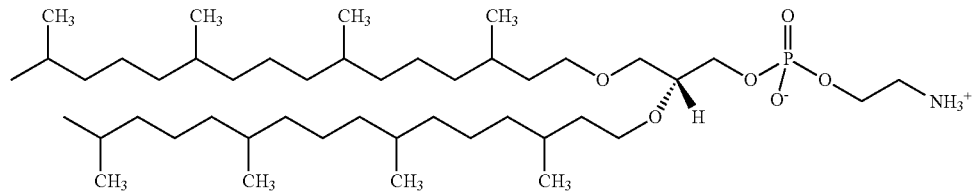 [SMILES: CC(C)CCCC(C)CCCC(C)CCCC(C)CCOC[C@H](COP(=O)([O-])OCC[NH3+])OCCC(C)CCCC(C)CCCC(C)CCCC(C)C]

1,2-di-O-phytanyl-sn-glycerol:

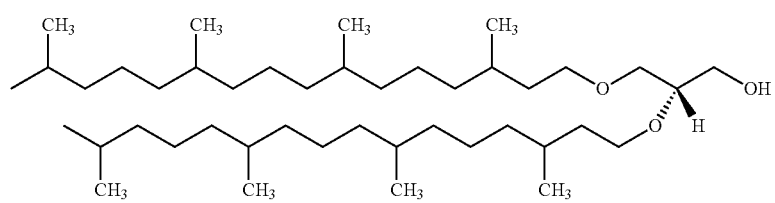 [SMILES: CC(C)CCCC(C)CCCC(C)CCCC(C)CCOC[C@H](CO)OCCC(C)CCCC(C)CCCC(C)CCCC(C)C]

Archaeobacteria that grow at extremely high temperatures are rich in diether and tetraether lipids. In thermoacidophiles or hyperthermophilic neutrophiles, the polar lipids contain diphytanylglycerol diether lipids (typically, ~5-10%) and dibiphytanylglycerol-tetraether lipids (typically ~90-95%, at optimum growth). The main phospholipid (the bipolar tetraether, GDGT, a caldarchaeol) of *Thermoplasma acidophilum* is commercially available from Matreya, LLC. The structure of this tetraether phospholipid is shown in Table 2.

TABLE 2

Glycerol dialkyl glycerol tetraether (GDGT)

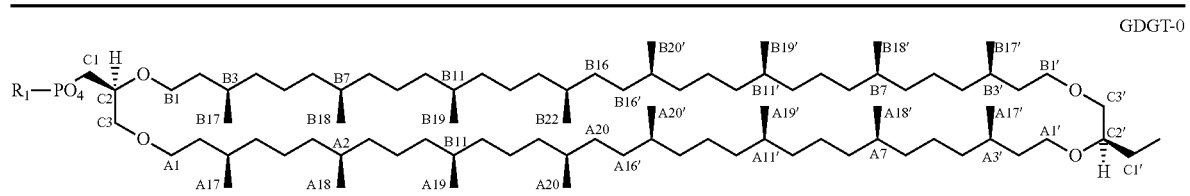

An ester-based phospholipid, 2-Oleoyl-1-palmitoyl-sn-glycero-3-phosphocholine (POPC), was used in parallel experiments. POPC has the structure shown in Table 3.

TABLE 3

2-Oleoyl-1-palmitoyl-sn-glycero-3-phosphocholine

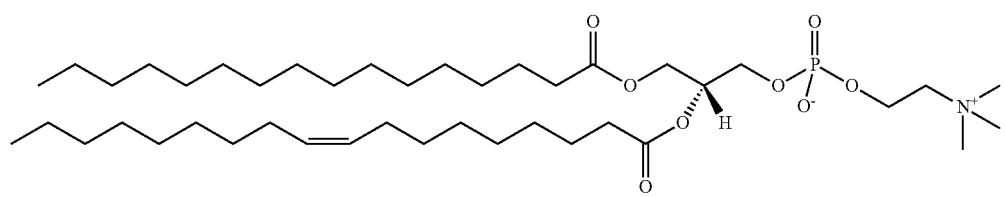 [SMILES: CCCCCCCC/C=C\CCCCCCCC(=O)O[C@H](COC(=O)CCCCCCCCCCCCCCC)COP(=O)([O-])OCC[N+](C)(C)C]

In such extreme thermophiles, the membrane is primarily composed of a single layer of bipolar tetraether lipids that span the entire membrane, rather than being organized as a lipid bilayer. This type of membrane structure confers additional stability at extreme temperatures. We construct nanodiscs that are analogous to those prepared with diether lipids using tetraether lipids. Additionally, mixtures of diether and tetraether lipids may still be useful to confer improved stability and/or immunopotency.

Nanodiscs were assembled with synthetic ester and ether lipids at select lipid:MSP ratio and temperature conditions selected based on the physical properties of the lipids and preliminary experiments. The fully assembled disc was purified from the unassembled proteins and lipids by Size Exclusion Chromatography.

The Following Stock and Working Solutions were Prepared:

A. Stock solution of 200 mM Na-cholate (17.22 g of sodium cholate (SAFC; Catalog #S1702-100G; Lot # SLBP3019V)) in 200 ml dI water. 0.22 µm filtered B. Stock solution of 5 M NaCl (146.1 g of sodium chloride (Fisher Chemical; Catalog # L-23125; Lot #144826A)) in 500 ml dI water. 0.22 µm filtered C. Stock solution of 10×TBS (Sigma; Catalog # T5912-1L; Lot # SLBN9754V)

D. Working solution of 100 mM Na-cholate+100 mM NaCl: 50 ml of (100 mM Sodium cholate+100 mM NaCl) solution was prepared by mixing 25 ml of 200 mM sodium cholate, 1 ml of 5 M NaCl and 24 ml dI water.

E. Working solution of 1×TBS: 100 ml 1×TBS was prepared by diluting 10 ml of 10×TBS in 90 ml dI water.

F. Working solution of 1×TBS+100 mM Na-cholate: 10 ml of buffer containing 1×TBS+100 mM Na-cholate was prepared by diluting 1 ml of 10×TBS and 200 mM Na-cholate in 4 ml dI water.

G. Lipids were as follows: POPC (Sigma; Catalog #42773-100MG; Lot # BCBQ7862V); 16:0 Diether PC* (Avanti Polar Lipids; Catalog #999992); and GDGT (Major phospholipid from *Thermoplasma acidophilum*) Matreya LLC; Catalog #1303; Lot #23412

2000 nmoles of lipids were aliquoted from chloroform stocks into 10-130 mm borosilicate test tubes and dried under a stream of pure Nitrogen to deposit a thin film of lipids on the walls of the tubes. The tubes were placed in a vacuum desiccator for 6-8 hours.

The dried lipids were removed from the desiccator and 40 µl of 100 mM sodium-cholate+100 mM NaCl buffer was added to each tube to reconstitute the lipids. The tubes were vortexed until no residue was seen on the walls of the tubes and sonicated for 30 minutes with intermittent vortexing in an 80 degrees F. water bath.

Reconstituted lipids were then mixed with 1×TBS and scaffold protein MSP1D1 (BioNanoCon, Lot #150221B or Sigma Catalog # M6574) and incubated at RT for 30 minutes. Disc reconstitution mixtures were prepared according to the recipe (all volumes in µl) shown in Table 4.

TABLE 4

| Disc reconstitution mixtures | | | | | |
|---|---|---|---|---|---|
| Lipid | 100 mM cholate + 100 mM NaCl | 1x TBS | 1x TBS + 100 mM cholate | MSP1D1 | TOTAL |
| POPC | 40 | 183 | 20 | 157 | 400 |
| POPC-PC* | 40 | 205 | 20 | 135 | 400 |

TABLE 4-continued

| Disc reconstitution mixtures | | | | | |
|---|---|---|---|---|---|
| Lipid | 100 mM cholate + 100 mM NaCl | 1x TBS | 1x TBS + 100 mM cholate | MSP1D1 | TOTAL |
| PC* | 40 | 96 | 0 | 114 | 250 |
| POPC-GDGT | 40 | 30 | 0 | 180 | 250 |

Detergent removal was achieved by direct addition of hydrophobic beads (AMBERLITE® XAD-2 beads (Rohm and Haas Co.)) to the disc reconstitution mixtures. A ratio of 50:1 (w/w) AMBERLITE® beads:detergent was used for detergent removal. Appropriate amount of dry AMBERLITE® XAD-2 beads (Rohm and Haas Co.) was weighed out in 2-ml microcentrifuge tubes with screw top caps, as shown in Table 5. After 5 hours of incubation at 37 degrees C. on a shaker, the AMBERLITE® beads were removed using a filter. Spent beads were washed with 1×TBS on the filter itself to make the total volume of each solution 600 Samples were stored at 4° C. until further use.

TABLE 5

| Detergent removal. | |
|---|---|
| Lipid | AMBERLITE® XAD-2 beads |
| POPC | 129 mg |
| POPC-PC* | 129 mg |
| PC* | 86 mg |
| POPC-GDGT | 86 mg |

The nanodiscs obtained from removing the AMBERLITE® beads (the filtrate) were purified using a SUPERDEX® 200 10/300 GL column (GE Healthcare Bio-Sciences A.B.) running 1×TBS at 0.75 ml/min. The purified nanodisc solution was stored at 4 degrees C. Purified nanodiscs were assessed using Size Exclusion Chromatography (SEC), as shown in FIG. 6A and FIG. 6B.

Figure 6A:
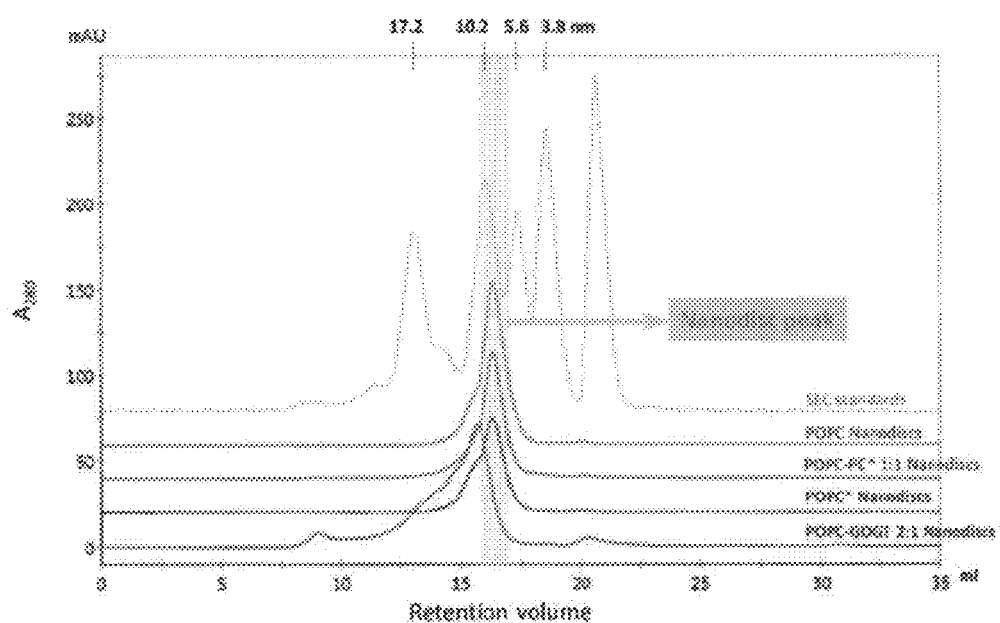
FIG. 6A shows a size exclusion chromatography plot showing the purification of ester and ether glycerophospholipid nanodiscs. The shaded band shows the nanodisc peak. Absorbance was measured at 280 nm.
Figure 6B:
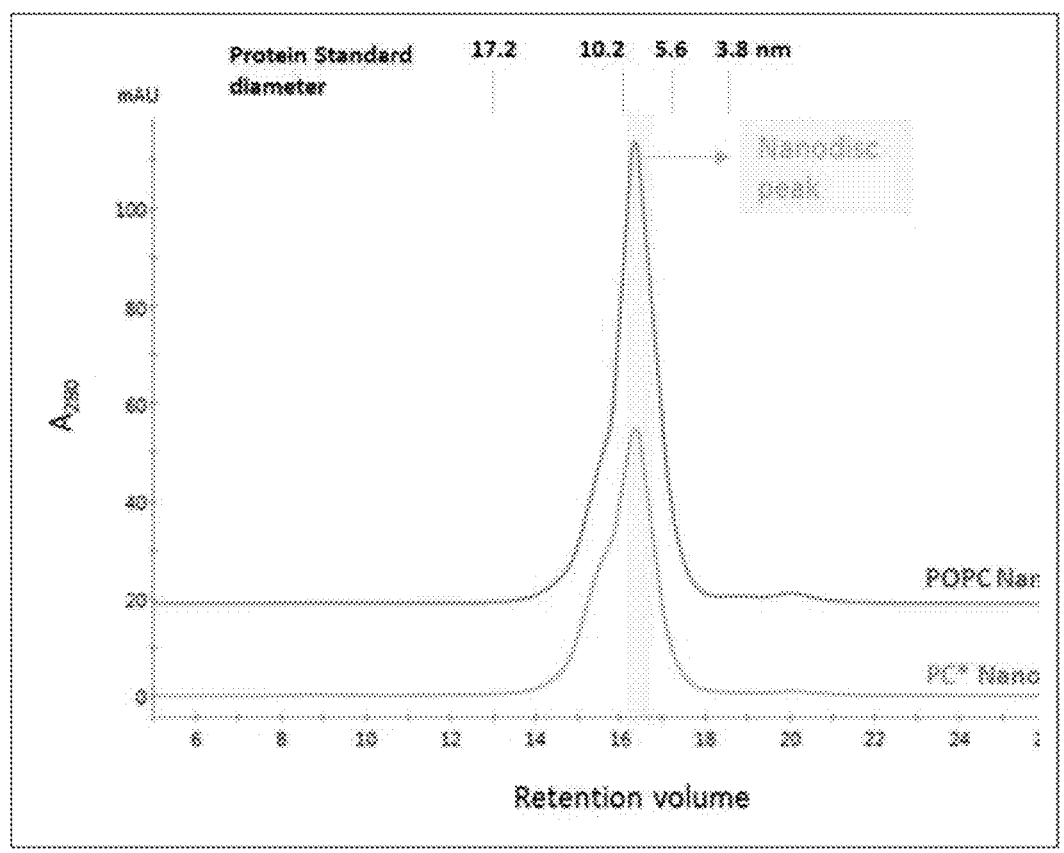
FIG. 6B shows a size exclusion chromatography plot showing the purification of ether glycerophospholipid POPC and PC* nanodiscs. The shaded band shows the nanodisc peak. Absorbance was measured at 280 nm.

FIGS. 6A and 6B shows the purification of PC* and POPC (control) nanodisc by SEC. The region of the peak highlighted in the shaded bar comprises of a homogenous, monodispersed population of nanodiscs and was used for further studies. POPC nanodiscs, which utilize phospholipids having an ester linkage between the phosphate and hydrophobic side chains, are described in U.S. Pat. No. 7,691,414, U.S. Pat. No. 7,662,410, U.S. Pat. No. 7,622,437, U.S. Pat. No. 7,592,008, U.S. Pat. No. 7,547,5763, U.S. Pat. No. 7,083,958, and U.S. Pat. No. 7,048,949. PC* nanodiscs comprise the thermostable, ether-linkage phospholipids.

The size exclusion chromatogram profile of PC* nanodiscs was very similar to that obtained for POPC Nanodiscs with identical retention volumes. Four fractions around the main peak which were expected to contain the well assembled nanodiscs were pooled (Table 6) and used for thermostability assessment. Amount determination was made by using an extinction coefficient at 280 nm of 0.8515 mg/ml.

TABLE 6

Fractions pooled from SEC purification

| ND composition | Fractions pooled | Volume (μl) | Conc. (mg/ml) | Amount (μg) |
|---|---|---|---|---|
| POPC | B7-B10 | 1930 | 0.30 | 592 |
| PC* | B7-B10 | 2000 | 0.18 | 364 |
| POPC:PC* | B7-B10 | 2000 | 0.22 | 442 |
| POPC-GDGT | B6-B9 | 2000 | 0.25 | 500 |

Example 5: Thermostability of POPC and PC* Nanodiscs

Purified POPC and PC* Nanodisc preparations were divided into 21 equal fractions, each in separate screw-top microcentrifuge tubes. Table 7 describes the pool fractions. Heat blocks were used for the study, and the nanodiscs were tested at room temperature, 37 degrees C., 50 degrees C., and 60 degrees C. Samples were taken at time zero (before heat exposure), and then after 30 minutes, 60 minutes, one hundred twenty minutes, twenty four hours, and forty eight hours of exposure to the heat conditions. All samples were analyzed at the same time at the end of the experiment. Samples were stored at 4° C. until that time.

TABLE 7

Pooled fractions for temperature stability.

| Disc type | Fractions pooled | Volume (μl) | Conc. (mg/ml) | Amount (μg) | Per sample amount | Per sample volume |
|---|---|---|---|---|---|---|
| POPC | 3B7-3B10 | 1930 | 0.30 | 571 | 27 | 92 |
| PC* | 3B7-3B10 | 2000 | 0.18 | 364 | 17 | 95 |
| POPC:PC* | 3B7-3B10 | 2000 | 0.22 | 442 | 21 | 95 |
| POPC-GDGT | 3B6-3B9 | 2000 | 0.25 | 500 | 24 | 95 |

Figure 7:
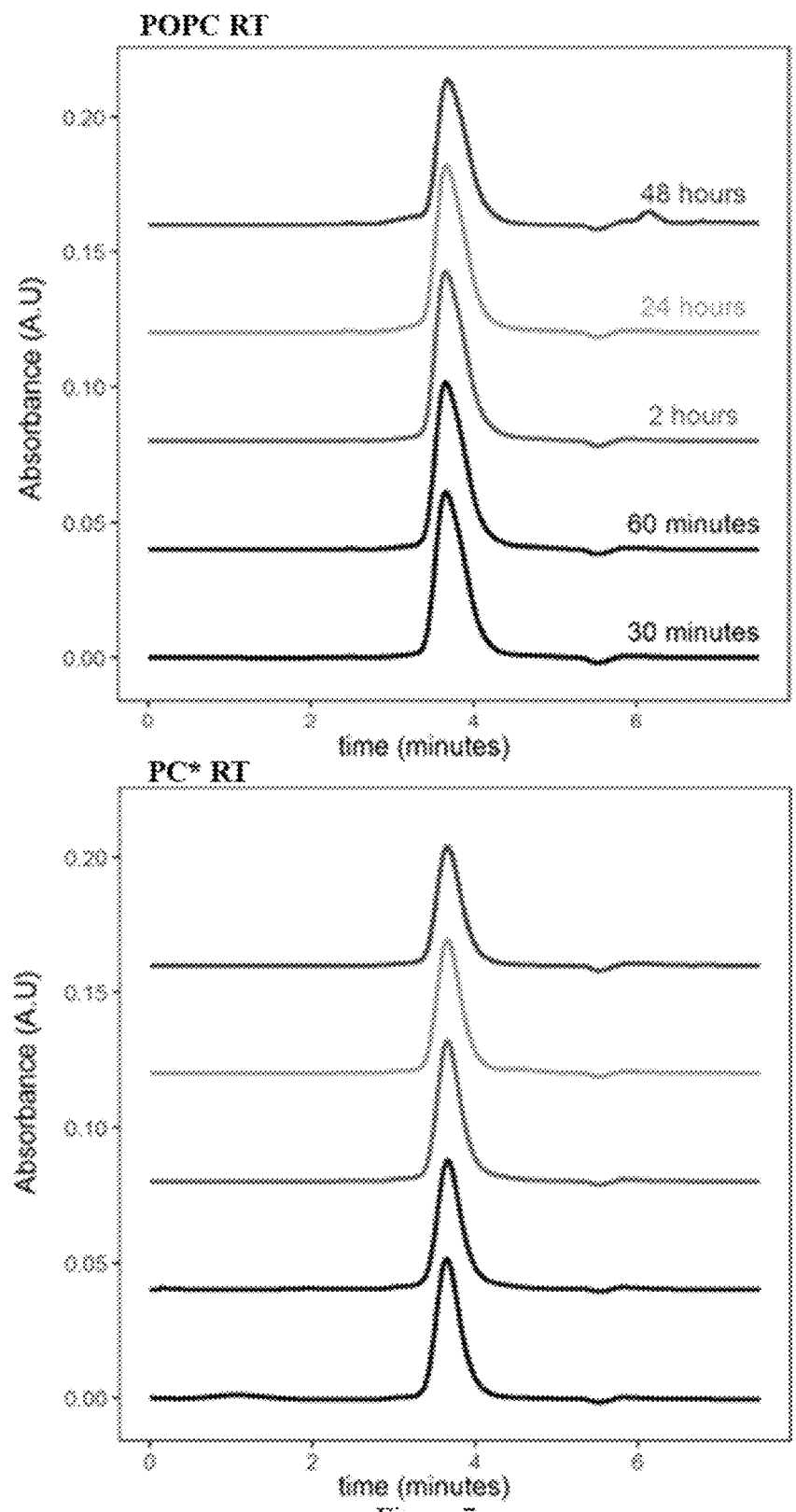
FIG. 7 shows size exclusion chromatography plots from thermostability testing of glycerophospholipid POPC and PC* nanodiscs at room temperature over the indicated time periods of (from top to bottom) 48 hours, 24 hours, 120 minutes, 60 minutes, and 30 minutes. POPC plots are shown in the left panel and PC* plots are shown in the right panel.
Figure 8:
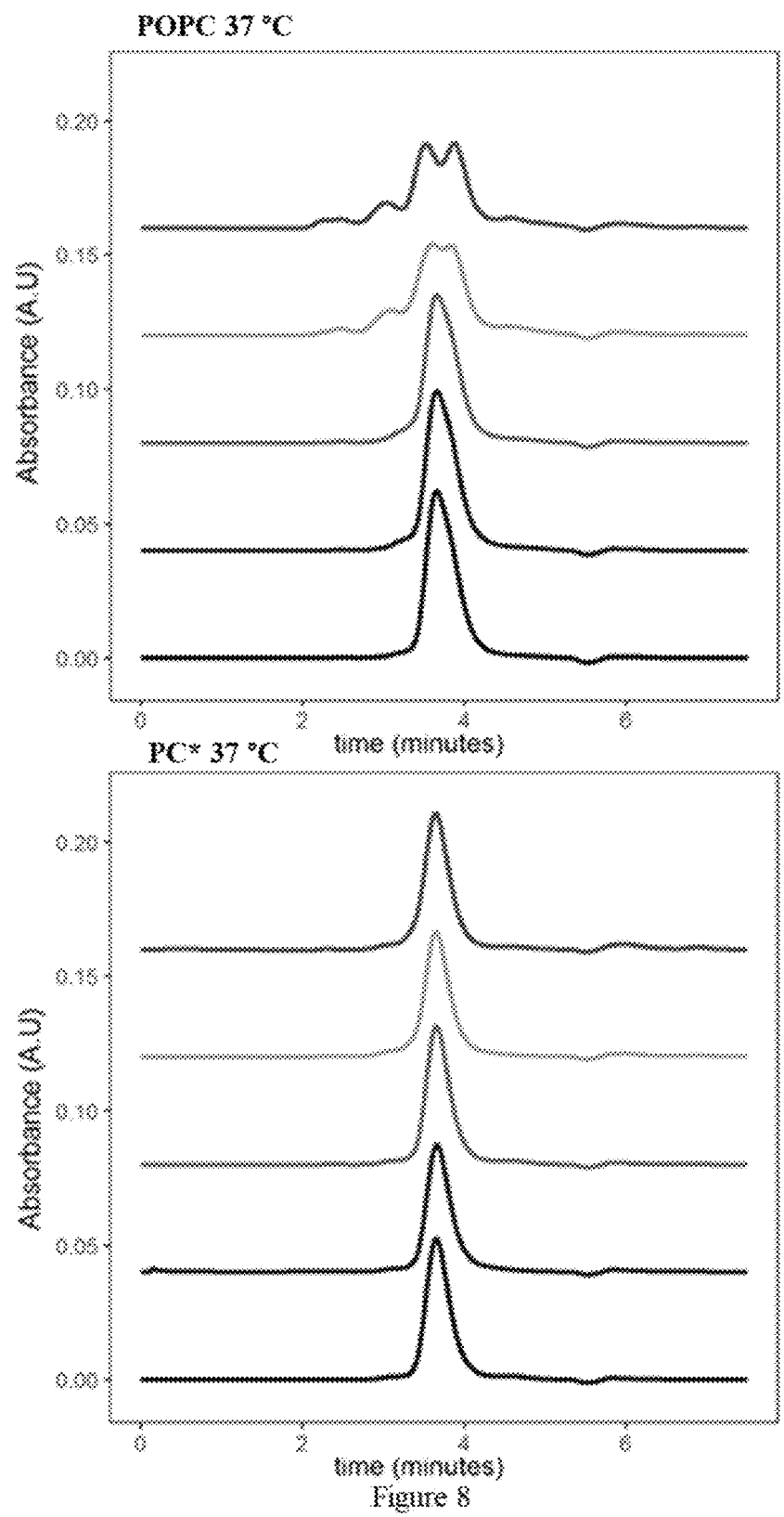
FIG. 8 shows size exclusion chromatography plots from thermostability testing of glycerophospholipid POPC and PC* nanodiscs at 37 degrees C. over the indicated time periods of (from top to bottom) 48 hours, 24 hours, 120 minutes, 60 minutes, and 30 minutes. POPC plots are shown in the left panel and PC* plots are shown in the right panel.

Samples were transferred to a 96-well plate and analyzed via Analytical SEC on a SUPERDEX® 200 Increase 5/150 GL column (GE Healthcare Bio-Sciences A.B.) running 100 mM sodium phosphate, 150 mM sodium chloride solution pH 7.2 at 0.45 ml/min Integrity of the main peak was used as a measure of thermostability and % area of the main peak was plotted against time for each sample to compare the thermostability of POPC and PC* nanodiscs at different temperatures. SEC-HPLC analytical data of pooled fractions are shown in FIG. 7 (POPC and PC* at room temperature), FIG. 8 (POPC and PC* at 37 degrees C.), FIG. 9 (POPC and PC* at 50 degrees C.), and FIG. 10 (POPC and PC* at 50 degrees C.). In the SEC plots, the main peak shows intact, thermostable nanodiscs while peaks to the left of the main peak show aggregates and other larger variants of the nanodiscs and peaks to the right of the main peak show breakdown products, fragments, and other small variants of the nanodiscs. The thermal stability profiles of the POPC and PC* nanodiscs is shown graphically in FIG. 11. Collectively, these data show that ether lipid nanodiscs (PC*) exhibit significantly higher tolerance to high temperatures relative to ester lipid nanodiscs (POPC). Thus, nanodiscs made with ether lipids are more thermostable and would impart thermostability to a membrane protein antigen inserted into such a nanodisc.

Example 6: Thermostability of GDGT Nanodiscs

Nanodiscs were prepared from GDGT by first drying thirty microliters of 42 nM GDGT lipids in 13×100 mm borosilicate tubes placed in a vacuum desiccator overnight. PC* lipid was dried in parallel. Dried GDGT lipid and dried PC* lipid each were reconstituted in 100 mM Na-cholate+ 100 mM NaCl according to Table 4. Each tube was vortexed for 30-60 seconds, then sonicated in an 80-100 degrees F. water bath for 15 minutes. Vortexing and sonication was repeated for three cycles with a 10 minute incubation period at room temperature before the last cycle. The tubes were then cooled to room temperature, and the lipids were mixed with MSP and buffer without cholate, then incubated at room temperature for 20 minutes with intermittent mixing by hand. Samples were then cleared of detergent via the addition of AMBERLITE® XAD-2 beads (Rohm and Haas Co.), followed by 5 hours of incubation, and removal of the beads via centrifugation and filtration. The nanodiscs were then subject to thermostability testing.

Example 7: Loading of Nanodiscs with Viral Antigens

Assembly of the thermostable nanodisc with an embedded vaccine antigen (e.g., microbial protein such as a viral envelope protein) involves mixing the protein of interest (vaccine antigen) with the membrane scaffolding protein(s) (MSP) and the thermostable phospholipids (e.g., that contain ether linkages) in an aqueous medium under conditions that promote self-assembly of the nanodiscs. Initially, the components are mixed together in an aqueous media containing a detergent, and then the detergent is removed. The nanodiscs then spontaneously assemble, with the antigen protein embedded in a bilayer of the phospholipids. In the assembled nanodisc, the antigen substantially retains its native conformation; the conditions attendant to mixing (including detergent exposure and temperature, even elevated temperatures), detergent removal, filtration, and assembly incubation do not substantially induce denaturing of the vaccine antigen protein.

The process of loading a nanodisc with a membrane glycoprotein (antigen) is similar to that of assembling empty nanodiscs. The protein of interest (e.g., Ebola GP) is first solubilized in a suitable detergent and then added to the disc reconstitution mixture—the mixture of phophoplipids, cholate and membrane scaffold protein (See, Example 4). The microbial protein (e.g., viral envelope protein such as Ebola GP) and the disc reconstitution mixture (phospholipids and MSP) is incubated for about 30 minutes to about an hour to ensure complete mixing. Detergent removal with the help of, for example, AMBERLITE® XAD-2 beads (Rohm & Haas Co.) initiates self-assembly, and the microbial protein is simultaneously self-assembled into the nanodisc—embedded in the bilayer of thermostable phospholipids.

Several key factors responsible for efficient incorporation of a membrane protein target into nanodiscs are to be considered, including—target solubilization detergent, lipid: MSP ratio and detergent removal rate. Detergents such as, but not limited to, ocytlglucoside, dodecyl maltoside, sodium cholate, TRITON® X-100, CHAPS and Fos-choline will be screened to identify conditions that best extract and solubilize monomeric GP from the viral membrane. A combination of size exclusion chromatography and SDS PAGE will be used to evaluate different solubilization conditions.

Depending on the type of lipid and MSP used, nanodiscs may require a particular ratio of phospholipids:MSP during formation for a complete assembly. When a microbial protein antigen is assembled into a nanodisc, the number of lipid molecules it will displace from the nanodisc is not known a priori. Following the identification of a suitable detergent for solubilization, the optimal phospholipid:MSP ratio for microbial protein incorporation would be empirically determined by assembling the protein at different phospholipid:MSP ratios, and identifying the ratio that results in a homogeneous SEC chromatogram.

A microbial protein may self-aggregate as the concentration of solubilizing detergent drops below its critical micellar concentration. Protein incorporation into nanodiscs depends on formation of correct contacts between the phospholipids and the protein as the detergent is being removed from the disc reconstitution mixture. Therefore, the rate of detergent removal is also a factor governing the efficiency of incorporation. Different weight ratios of detergent removal beads (e.g., AMBERLITE® beads) to total detergent used during nanodisc assembly will be used to perform assembly, and the efficiency of incorporation will be determined by comparing the amount of microbial protein (e.g., viral envelope protein) in the assembly mixture and the final nanodisc preparation based on SDS-PAGE and antibody based detection methods such as ELISA and Western blotting.

The approach outlined above been used to optimize incorporation of several membrane proteins into Nanodiscs including recombinant Hemagglutinin from H1N1 and gp-160 from HIV. See, Bayburt, T H et al. (2010) FEBS Letters, 584:1721-7; Bhattacharya, P et al. (2010) J. Virol. 84:361-71; and Nakatani-Webster, E et al. (2015) J. Virol. Methods, 226:15-24.

Figure 5:
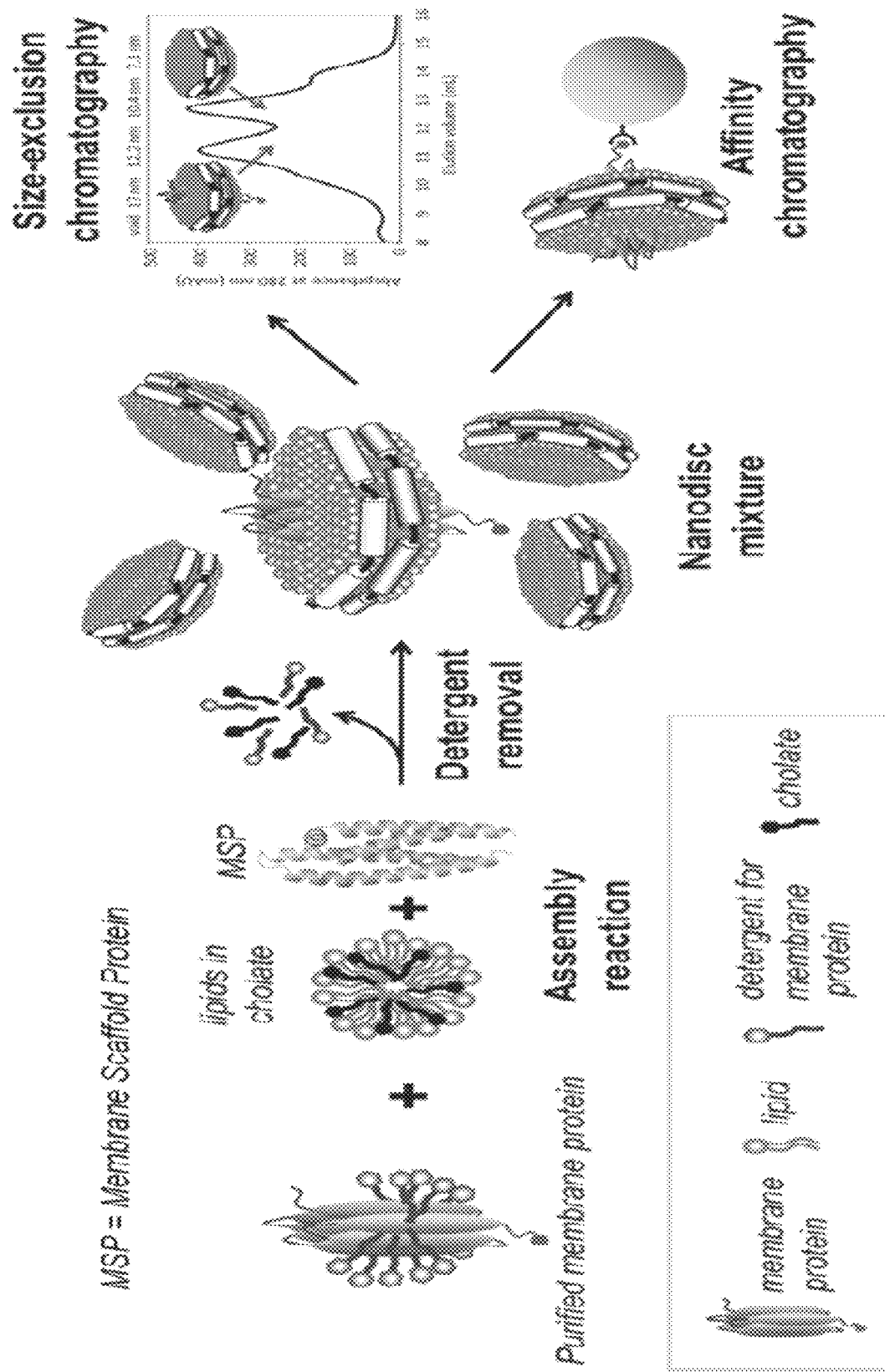
FIG. 5 shows a strategy for assembling nanodiscs by mixing all the components and then initiating self-assembly of the discoid nanodisc structures by removing the detergent(s). As shown, a purified membrane protein such as a viral envelope protein, which has been solubilized with its optimally appropriate detergent, is combined with lipid/cholate micelles and a Membrane Scaffold Protein (MSP). Removal of the detergent can be accomplished by any of several different procedures, for example, by adsorbing the detergent to commercially available beads designed for that purpose. Nanodiscs form spontaneously, and the next hurdle is to separate ones containing the envelope protein from those without it. Size exclusion chromatography (SEC) and affinity chromatography are commonly used to recover nanodiscs with an embedded membrane protein.

The loading of vaccine antigen proteins into the nanodisc is illustrated in FIG. 5. The process exploits the propensity of the nanodiscs to auto-assemble when detergent is slowly removed from a combination of the protein antigen, membrane scaffold protein (MSP), and phospholipids.

Example 8: Test Lyophilized Nanodiscs to Demonstrate their In Vivo Immunogenic Potential The ability of the nanodiscs to generate a protective immune response is tested in a mouse model using challenge with ma-Ebola. Groups of ten mice are inoculated three times with varying doses of vaccine, up to 20 microgram GP content, with two weeks between injections. Nano-VLPs are used as positive control. Anti-GP titers are measured by ELISA. Survival to challenge after 10 days is the key metric of success. If the nanodisc approach proves to be successful, as defined by exhibiting immunopotency at least comparable to that of Nano-VLPs, guinea pig studies are initiated.

Example 9: Assembly of rHA in Nanodiscs

A procedure for the assembly of a membrane protein antigen, recombinant hemagglutinin from H1N1 A/New Caledonia/20/99 in this case, into ester and ether-based Nanodiscs and their characterization is described.

A. Assembly of rHA in MSP1D1-POPC Nanodiscs

Assembly of a membrane protein antigen into Nanodiscs involves combining detergent solubilized membrane protein, lipids and membrane scaffold protein (MSP) in specific ratios and incubating the mixture with hydrophobic beads to remove the detergent. Detergent removal initiates self-assembly of the membrane protein of interest into Nanodiscs. Antigen-Nanodiscs may be separated from unincorporated antigen, empty discs and surplus lipid and MSP mixture by the application of appropriate chromatographic purification steps such as affinity chromatography and size exclusion chromatography.

Procedure for rHA Nanodisc Assembly:

1820 nmoles of PC phospholipid (1-palmitoyl-2-oleoyl-sn-glycero-3-phosphocholine, Avanti Polar Lipids; Catalog #850457) were dried under a stream of pure Nitrogen and reconstituted in 36.4 μl of 100 mM sodium-cholate (SAFC; Catalog #S1702-100G; Lot #SLPB3019V)+100 mM NaCl buffer followed by intermittent vortexing and sonication in a 30° C. water bath for 30 minutes.

Separately, 68.5 μl of 598.5 mM β-OG (n-octyl-β-D-glucopyranoside; Anatrace; Catalog #O311; Lot #69360)+300 mM NaCl solution was added to 400 μl of recombinant hemagglutinin (rHA) (Protein Sciences, Catalog #3006; Lot #1368-133) and the rHA detergent mixture was placed on a shaker platform at 4° C. for 1 hour.

Disc reconstitution mixture was prepared by adding 159 μl of 176.6 μM MSP1D1 (BioNanoCon; Lot #150221B), 36.4 μl of 200 mM sodium cholate and 40 μl of 20% (w/v) β-OG to the cholate solubilized lipids. 455 μl of β-OG solubilized rHA was added to the disc reconstitution mixture (DRM). The final volume was adjusted to 728 μl using buffer (50 mM sodium phosphate pH 7.2+150 mM NaCl) and the mixture incubated on ice with gentle shaking for 1 hour. The final concentrations of lipids, sodium cholate, β-OG, MSP1D1 and rHA in the mixture were 2.5 mM, 15.0 mM, 87.5 mM, 38.5 μM and 1.9 μM respectively.

After an hour of incubation, 305 mg of Biobeads SM-2 (BioRad; Catalog #152-3920; Lot #64037853; Exp: 2016 Jan. 26) were added to the mix and the tube was incubated on ice for another 2 hours. Biobeads were rinsed with buffer before use. After 2 hours, Biobeads were removed and rinsed with 400 μl buffer twice. The Nanodisc solution and the wash were combined and filtered through a 0.22 μm filter. The mixture was then purified via SEC. Column used: Superdex 200 Inc. 10/300 GL (GE Healthcare; Code #28-9909-44; Lot #10226065; Exp: 2019 June, ID: 0121). 0.22 μm filtered 50 mM sodium phosphate pH 7.2+150 mM NaCl was used as the running buffer.

The disc assembly process described above results in the formation of rHA monomers, dimers and trimers in Nanodiscs. FIG. 12 shows theoretical retention volumes of these three species on a Superdex 200 Increase 10-300 GL size exclusion chromatography (SEC) column.

SEC fractions from the purification of rHA Nanodiscs were analyzed for their rHA and MSP content using a densitometric analysis of individual SEC fractions on an SDS PAGE gel. Total protein load was normalized to 0.5 μg. FIG. 13 shows the SEC chromatogram of the rHA-Nanodisc mixture. The major peak at 16.76 ml represents empty Nanodiscs, originating from the excess of disc reconstitution mixture used during assembly.

Characterization of rHA Nanodiscs Using SDS-PAGE:

FIG. 14 shows the SDS PAGE gel of SEC fractions from rHA Nanodisc purification as described above. (Protein standards). Lane 11 consists of MSP1D1, a 25 kDa protein showing up as a single band. Lane 12 contains rHA showing up as three bands having molecular weights of ~70, 140 and 210 kDa. Fractions B1 through B9 show varying amounts of protein bands corresponding to rHA and MSP1D1. A densitometric analysis of lanes 1-9 reveals the ratio of rHA: MSP in these fractions. Each Nanodisc is composed of two MSP molecules and hence, an 'rHA: Nanodisc' ratio can be derived from these values. For rHA, the sum of intensities of bands at 70, 140 and 210 kDa was used. Fractions B1-B9 show ratios of rHA: ND ranging from 3 to 1 indicating the three different rHA:ND populations (Table 8). FIG. 15 represents this pictorially.

TABLE 8

Densitometric analysis of SDS-PAGE of SEC fractions
from purification of POPC based rHA-Nanodiscs

| | | rHA | | | | MSP | rHA | rHA |
|---|---|---|---|---|---|---|---|---|
| Lane | Sample | Band 1 | Band 2 | Band 3 | Band 1 + 2 + 3 | Band 4 | Total:MSP | Total:ND |
| 1 | B1 | 1259359 | 2327569 | 3379594 | 6966522 | | | |
| 2 | B2 | 2372706 | 3362373 | 4650660 | 10385739 | 1767843 | 5.9 | 2.9 |
| 3 | B3 | 2030994 | 2915892 | 4274550 | 9221436 | 1988217 | 4.6 | 2.3 |
| 4 | B4 | 1529829 | 3578778 | 4597299 | 9705906 | 2699298 | 3.6 | 1.8 |
| 5 | B5 | 1521920 | 3876304 | 4105658 | 9503882 | 3384222 | 2.8 | 1.4 |
| 6 | B6 | 2117360 | 5041080 | 5244912 | 12403352 | 4895008 | 2.5 | 1.3 |
| 7 | B7 | 2966647 | 5252569 | 10255259 | 18474475 | 8770220 | 2.1 | 1.1 |
| 8 | B8 | 2759988 | 2987580 | 8332338 | 14079906 | 14047803 | 1.0 | 0.5 |
| 9 | B9 | — | — | — | — | 25338240 | | |
| 10 | MWM | — | — | — | — | — | | |
| 11 | MSP | — | — | — | — | 38202678 | | |
| 12 | rHA | 3548288 | 5432252 | 12051776 | 21032316 | — | | |

In Vitro Hemagglutination Assay on rHA ND SEC Fractions:

To confirm that rHA in Nanodiscs is active, an in vitro hemagglutination assay was performed. Briefly, 7-two-fold dilutions of SEC fractions B1-B9 were prepared in a 96-wells plate starting at 25 µg/ml. An equal volume of 0.6% chicken red blood cells (Lampire Biological Laboratories; Catalog #7241409; Lot #16K28200) in PBS was added to each well and the contents mixed thoroughly with the help of a pipette. 1×PBS and empty ND show settling of cell suspension indicating the lack of agglutination. FIG. 16 shows the hemagglutination results. rHA control showed agglutination for all dilutions tested. The HI titer for rHA is not known and needs to be determined empirically or found from literature. All rHA ND fractions show agglutination with different titers. Additionally, the titer value for rHA-ND fractions follow the HA: ND ratios in these fractions as determined by SDS-PAGE.

B. Assembly of rHA in 16:0 Ether PC Nanodiscs

Procedure for rHA Nanodisc Assembly:

25 µl of 50 mg/ml 16:0 diether PC (1,2-di-0-hexadecyl-sn-glycero-3-phosphocholine, Avanti Polar Lipids, Catalog #999992, Lot #160DEPC-14) was dried under a stream of pure nitrogen and reconstituted in 35.4 µl of 100 mM sodium-cholate (SAFC; Catalog #S1702-100G; Lot #SLPB3019V)+100 mM NaCl buffer followed by intermittent vortexing and sonication in a 30° C. water bath for 30 minutes.

Separately, 150.4 µl of 598.5 mM β-OG (n-octyl-β-D-glucopyranoside; Anatrace; Catalog #0311; Lot #69360)+ 300 mM NaCl solution was added to 1050 µl of recombinant hemagglutinin (Protein Sciences, Catalog #3006_H1_NC; Lot #1368-133) and the rHA detergent mixture was placed on a shaker platform at 4° C. for 1 hour.

Disc reconstitution mixture was prepared by adding 103.4 µl of 190.2 µM MSP1D1 (BioNanoCon; Lot #150221B), 58.2 µl of 200 mM sodium cholate and 40.4 µl of 20% (w/v) β-OG to the cholate solubilized lipids. 446 µl of β-OG solubilized rHA was added to the disc reconstitution mixture (DRM). The final volume was adjusted to 842.9 µl using buffer (100 mM sodium phosphate pH 7.4+150 mM NaCl) and the mixture incubated on a shaker platform with gentle shaking for 30 minutes. The final concentrations of lipids, sodium cholate, β-OG, MSP1D1 and rHA in the mixture were 2.1 mM, 18.0 mM, 75.0 mM, 23.3 µM and 1.7 µM respectively.

After an hour of incubation, 760 mg of Amberlite® XAD®-2 (Sigma-Aldrich; Catalog #10357) were added to the DRM and the tube was incubated at 37° C. for 2 hours followed by an hour-long incubation 25° C. After the incubation, Amberlite beads were removed and rinsed with 1 ml buffer. The Nanodisc solution and the wash were combined and filtered through a 0.22 µm filter. The mixture was then purified via SEC. Column used: Superdex 200 Inc. 10/300 GL (GE Healthcare; Code #28-9909-44; Lot #10226065; Exp: 2019-06, ID: 0121). 0.22 µm filtered, 100 mM sodium phosphate pH 7.4+150 mM NaCl was used as the running buffer.

The disc assembly process described above results in the formation of rHA monomers, dimers and trimers in Nanodiscs. FIG. 12 shows theoretical retention volumes of these three species on a Superdex 200 Increase 10-300 GL size exclusion chromatography (SEC) column. FIG. 17 shows the SEC chromatogram of the rHA-Nanodisc mixture.

Characterization:

FIG. 18 shows the SDS PAGE gel of SEC fractions from rHA Nanodisc purification as described above. Lane 11 consists of MSP1D1, a 25 kDa protein showing up as a single band. Lane 12 contains rHA showing up as three bands having molecular weights of ~70, 140 and 210 kDa. Fractions B1 through B9 show protein bands corresponding to both rHA and MSP1D1 indicating successful formation of Nanodiscs containing incorporated rHA. A densitometric analysis of lanes 1-9 reveals the ratio of rHA: MSP in these fractions. Each Nanodisc is composed of two MSP molecules and hence, an 'rHA: Nanodisc' ratio can be derived from these values. For rHA, the sum of intensities of bands at 70, 140 and 210 kDa was used. Fractions B1-B9 show ratios of rHA: ND ranging from 3 to 1 indicating the three different rHA: ND populations (Table 9). FIG. 19 provides a pictorial representation of this observation.

TABLE 9

Densitometric analysis of SDS-PAGE of SEC fractions from purification of 16:0ePC based rHA-Nanodiscs

| Lane | Sample | rHA Band 1 | rHA Band 2 | rHA Band 3 | rHA Band 4 | rHA Total | MSP Band 5 | rHA total:MSP | rHA total:ND |
|---|---|---|---|---|---|---|---|---|---|
| 1 | B1 | 898703 | 2589164 | 5606619 | — | 9094486 | 7284159 | 1 | 2 |
| 2 | B2 | 1727472 | 4725874 | 8208777 | — | 14662123 | 10412501 | 1 | 3 |
| 3 | B3 | 2402941 | 4828293 | 8444056 | — | 15675290 | 10013483 | 2 | 3 |
| 4 | B4 | 2351330 | 4859683 | 9429556 | — | 16640569 | 10554924 | 2 | 3 |
| 5 | B5 | 2510032 | 5106350 | 7600103 | — | 15216485 | 13577197 | 1 | 2 |
| 6 | B6 | 3849071 | 4159613 | 9244720 | 1501902 | 18755306 | 21841235 | 1 | 2 |
| 7 | B7 | 3501810 | 2826925 | 7950284 | 3021689 | 17300708 | 29438637 | 1 | 1 |
| 8 | B8 | 1746598 | 906806 | 2454990 | 2273366 | 7381760 | 29431191 | 0 | 1 |
| 9 | B9 | — | — | — | 1251658 | 1251658 | 43953519 | 0 | 0 |
| 10 | MWM | — | — | — | — | — | — | | |
| 11 | MSP | — | — | — | — | — | 55336555 | | |
| 12 | rHA | 3410560 | 6182151 | 10546602 | 22743661 | 42882974 | — | | |

We have shown here that purified recombinant hemagglutinin can be assembled into Nanodiscs using both ester and ether-based lipids, POPC and 16:0 dietherPC respectively. In vitro, hemagglutination analysis shows that rHA in Nanodiscs is functionally active Disc assembly results in formation of all-trimeric, dimeric and monomeric forms of rHA, present in separate fractions of a size-exclusion chromatrography purification run, thus allowing a precise control on

```
                195                 200                 205

Asn Thr Gln
    210

<210> SEQ ID NO 2
<211> LENGTH: 190
<212> TYPE: PRT
<213> ORGANISM: Homo sapiens

<400> SEQUENCE: 2

Gly Ser Thr Phe Ser Lys Leu Arg Glu Gln Leu Gly Pro Val Thr Gln
1               5                   10                  15

Glu Phe Trp Asp Asn Leu Glu Lys Glu Thr Glu Gly Leu Arg Gln Glu
            20                  25                  30

Met Ser Lys Asp Leu Glu Glu Val Lys Ala Lys Val Gln Pro Tyr Leu
        35                  40                  45

Asp Asp Phe Gln Lys Lys Trp Gln Glu Glu Met Glu Leu Tyr Arg Gln
    50                  55                  60

Lys Val Glu Pro Leu Arg Ala Glu Leu Gln Glu Gly Ala Arg Gln Lys
65                  70                  75                  80

Leu His Glu Leu Gln Glu Lys Leu Ser Pro Leu Gly Glu Glu Met Arg
                85                  90                  95

Asp Arg Ala Arg Ala His Val Asp Ala Leu Arg Thr His Leu Ala Pro
            100                 105                 110

Tyr Ser Asp Glu Leu Arg Gln Arg Leu Ala Ala Arg Leu Glu Ala Leu
        115                 120                 125

Lys Glu Asn Gly Gly Ala Arg Leu Ala Glu Tyr His Ala Lys Ala Thr
    130                 135                 140

Glu His Leu Ser Thr Leu Ser Glu Lys Ala Lys Pro Ala Leu Glu Asp
145                 150                 155                 160

Leu Arg Gln Gly Leu Leu Pro Val Leu Glu Ser Phe Lys Val Ser Phe
                165                 170                 175

Leu Ser Ala Leu Glu Glu Tyr Thr Lys Lys Leu Asn Thr Gln
            180                 185                 190

<210> SEQ ID NO 3
<211> LENGTH: 233
<212> TYPE: PRT
<213> ORGANISM: Homo sapiens

<400> SEQUENCE: 3

Gly His His His His His His Asp Tyr Asp Ile Pro Thr Thr Glu
1               5                   10                  15

Asn Leu Tyr Phe Gln Gly Ser Thr Phe Ser Lys Leu Arg Glu Gln Leu
            20                  25                  30

Gly Pro Val Thr Gln Glu Phe Trp Asp Asn Leu Glu Lys Glu Thr Glu
        35                  40                  45

Gly Leu Arg Gln Glu Met Ser Lys Asp Leu Glu Glu Val Lys Ala Lys
    50                  55                  60

Val Gln Pro Tyr Leu Asp Asp Phe Gln Lys Lys Trp Gln Glu Glu Met
65                  70                  75                  80

Glu Leu Tyr Arg Gln Lys Val Glu Pro Leu Arg Ala Glu Leu Gln Glu
                85                  90                  95

Gly Ala Arg Gln Lys Leu His Glu Leu Gln Glu Lys Leu Ser Pro Leu
            100                 105                 110

Arg Ala Glu Leu Gln Glu Gly Ala Arg Gln Lys Leu His Glu Leu Gln
```

```
                115              120              125
Glu Lys Leu Ser Pro Leu Gly Glu Glu Met Arg Asp Arg Ala Arg Ala
            130              135              140

His Val Asp Ala Leu Arg Thr His Leu Ala Pro Tyr Ser Asp Glu Leu
145              150              155              160

Arg Gln Arg Leu Ala Ala Arg Leu Glu Ala Leu Lys Glu Asn Gly Gly
                165              170              175

Ala Arg Leu Ala Glu Tyr His Ala Lys Ala Thr Glu His Leu Ser Thr
            180              185              190

Leu Ser Glu Lys Ala Lys Pro Ala Leu Glu Asp Leu Arg Gln Gly Leu
                195              200              205

Leu Pro Val Leu Glu Ser Phe Lys Val Ser Phe Leu Ser Ala Leu Glu
210              215              220

Glu Tyr Thr Lys Lys Leu Asn Thr Gln
225              230
```

<210> SEQ ID NO 4
<211> LENGTH: 232
<212> TYPE: PRT
<213> ORGANISM: Homo sapiens

<400> SEQUENCE: 4

```
Gly His His His His His Asp Tyr Asp Ile Pro Thr Thr Glu Asn
1                5                10               15

Leu Tyr Phe Gln Gly Ser Thr Phe Ser Lys Leu Arg Glu Gln Leu Gly
                20               25               30

Pro Val Thr Gln Glu Phe Trp Cys Asn Leu Glu Lys Glu Thr Glu Gly
            35               40               45

Leu Arg Gln Glu Met Ser Lys Asp Leu Glu Glu Val Lys Ala Lys Val
50               55               60

Gln Pro Tyr Leu Asp Asp Phe Gln Lys Lys Trp Gln Glu Glu Met Glu
65               70               75               80

Leu Tyr Arg Gln Lys Val Glu Pro Tyr Leu Asp Asp Phe Gln Lys Lys
                85               90               95

Trp Gln Glu Glu Met Glu Leu Tyr Arg Gln Lys Val Glu Pro Leu Arg
            100              105              110

Ala Glu Leu Gln Glu Gly Ala Arg Gln Lys Leu His Glu Leu Gln Glu
        115              120              125

Lys Leu Ser Pro Leu Gly Glu Glu Met Arg Asp Arg Ala Arg Ala His
    130              135              140

Val Asp Ala Leu Arg Thr His Leu Ala Pro Tyr Ser Asp Glu Leu Arg
145              150              155              160

Gln Arg Leu Ala Ala Arg Leu Glu Ala Leu Lys Glu Asn Gly Gly Ala
                165              170              175

Arg Leu Ala Glu Tyr His Ala Lys Ala Thr Glu His Leu Ser Thr Leu
            180              185              190

Ser Glu Lys Ala Lys Pro Ala Leu Glu Asp Leu Arg Gln Gly Leu Leu
        195              200              205

Pro Val Leu Glu Ser Phe Lys Val Ser Phe Leu Ser Ala Leu Glu Glu
210              215              220

Tyr Thr Lys Lys Leu Asn Thr Gln
225              230
```

<210> SEQ ID NO 5
<211> LENGTH: 255

```
<212> TYPE: PRT
<213> ORGANISM: Homo sapiens

<400> SEQUENCE: 5

Gly His His His His His His Asp Tyr Asp Ile Pro Thr Thr Glu
1               5                   10                  15

Asn Leu Tyr Phe Gln Gly Ser Thr Phe Ser Lys Leu Arg Glu Gln Leu
            20                  25                  30

Gly Pro Val Thr Gln Glu Phe Trp Asp Asn Leu Glu Lys Glu Thr Glu
            35                  40                  45

Gly Leu Arg Gln Glu Met Ser Lys Asp Leu Glu Glu Val Lys Ala Lys
        50                  55                  60

Val Gln Pro Tyr Leu Asp Asp Phe Gln Lys Lys Trp Gln Glu Glu Met
65                  70                  75                  80

Glu Leu Tyr Arg Gln Lys Val Glu Pro Leu Arg Ala Glu Leu Gln Glu
            85                  90                  95

Gly Ala Arg Gln Lys Leu His Glu Leu Gln Glu Lys Leu Ser Pro Tyr
            100                 105                 110

Leu Asp Asp Phe Gln Lys Lys Trp Gln Glu Glu Met Glu Leu Tyr Arg
            115                 120                 125

Gln Lys Val Glu Pro Leu Arg Ala Glu Leu Gln Glu Gly Ala Arg Gln
            130                 135                 140

Lys Leu His Glu Leu Gln Glu Lys Leu Ser Pro Leu Gly Glu Glu Met
145                 150                 155                 160

Arg Asp Arg Ala Arg Ala His Val Asp Ala Leu Arg Thr His Leu Ala
                165                 170                 175

Pro Tyr Ser Asp Glu Leu Arg Gln Arg Leu Ala Ala Arg Leu Glu Ala
            180                 185                 190

Leu Lys Glu Asn Gly Gly Ala Arg Leu Ala Glu Tyr His Ala Lys Ala
            195                 200                 205

Thr Glu His Leu Ser Thr Leu Ser Glu Lys Ala Lys Pro Ala Leu Glu
        210                 215                 220

Asp Leu Arg Gln Gly Leu Leu Pro Val Leu Glu Ser Phe Lys Val Ser
225                 230                 235                 240

Phe Leu Ser Ala Leu Glu Glu Tyr Thr Lys Lys Leu Asn Thr Gln
                245                 250                 255

<210> SEQ ID NO 6
<211> LENGTH: 254
<212> TYPE: PRT
<213> ORGANISM: Homo sapiens

<400> SEQUENCE: 6

Gly His His His His His His Asp Tyr Asp Ile Pro Thr Thr Glu Asn
1               5                   10                  15

Leu Tyr Phe Gln Gly Ser Thr Phe Ser Lys Leu Arg Glu Gln Leu Gly
            20                  25                  30

Pro Val Thr Gln Glu Phe Trp Cys Asn Leu Glu Lys Glu Thr Glu Gly
            35                  40                  45

Leu Arg Gln Glu Met Ser Lys Asp Leu Glu Glu Val Lys Ala Lys Val
        50                  55                  60

Gln Pro Tyr Leu Asp Asp Phe Gln Lys Lys Trp Gln Glu Glu Met Glu
65                  70                  75                  80

Leu Tyr Arg Gln Lys Val Glu Pro Leu Arg Ala Glu Leu Gln Glu Gly
            85                  90                  95
```

Ala Arg Gln Lys Leu His Glu Leu Gln Glu Lys Leu Ser Pro Tyr Leu
            100                 105                 110

Asp Asp Phe Gln Lys Lys Trp Gln Glu Met Glu Leu Tyr Arg Gln
            115                 120                 125

Lys Val Glu Pro Leu Arg Ala Glu Leu Gln Glu Gly Ala Arg Gln Lys
        130                 135                 140

Leu His Glu Leu Gln Glu Lys Leu Ser Pro Leu Gly Glu Glu Met Arg
145                 150                 155                 160

Asp Arg Ala Arg Ala His Val Asp Ala Leu Arg Thr His Leu Ala Pro
                165                 170                 175

Tyr Ser Asp Glu Leu Arg Gln Arg Leu Ala Ala Arg Leu Glu Ala Leu
            180                 185                 190

Lys Glu Asn Gly Gly Ala Arg Leu Ala Glu Tyr His Ala Lys Ala Thr
        195                 200                 205

Glu His Leu Ser Thr Leu Ser Glu Lys Ala Lys Pro Ala Leu Glu Asp
    210                 215                 220

Leu Arg Gln Gly Leu Leu Pro Val Leu Glu Ser Phe Lys Val Ser Phe
225                 230                 235                 240

Leu Ser Ala Leu Glu Glu Tyr Thr Lys Lys Leu Asn Thr Gln
                245                 250

<210> SEQ ID NO 7
<211> LENGTH: 276
<212> TYPE: PRT
<213> ORGANISM: Homo sapiens

<400> SEQUENCE: 7

Gly His His His His His Asp Tyr Asp Ile Pro Thr Thr Glu Asn
1               5                   10                  15

Leu Tyr Phe Gln Gly Ser Thr Phe Ser Lys Leu Arg Glu Gln Leu Gly
            20                  25                  30

Pro Val Thr Gln Glu Phe Trp Cys Asn Leu Glu Lys Glu Thr Glu Gly
        35                  40                  45

Leu Arg Gln Glu Met Ser Lys Asp Leu Glu Glu Val Lys Ala Lys Val
50                  55                  60

Gln Pro Tyr Leu Asp Asp Phe Gln Lys Lys Trp Gln Glu Glu Met Glu
65                  70                  75                  80

Leu Tyr Arg Gln Lys Val Glu Pro Leu Arg Ala Glu Leu Gln Glu Gly
                85                  90                  95

Ala Arg Gln Lys Leu His Glu Leu Gln Glu Lys Leu Ser Pro Leu Gly
            100                 105                 110

Glu Glu Met Arg Asp Arg Ala Arg Ala His Val Asp Ala Leu Arg Thr
        115                 120                 125

His Leu Ala Pro Tyr Leu Asp Asp Phe Gln Lys Lys Trp Gln Glu Glu
130                 135                 140

Met Glu Leu Tyr Arg Gln Lys Val Glu Pro Leu Arg Ala Glu Leu Gln
145                 150                 155                 160

Glu Gly Ala Arg Gln Lys Leu His Glu Leu Gln Glu Lys Leu Ser Pro
                165                 170                 175

Leu Gly Glu Glu Met Arg Asp Arg Ala Arg Ala His Val Asp Ala Leu
            180                 185                 190

Arg Thr His Leu Ala Pro Tyr Ser Asp Glu Leu Arg Gln Arg Leu Ala
        195                 200                 205

Ala Arg Leu Glu Ala Leu Lys Glu Asn Gly Gly Ala Arg Leu Ala Glu
    210                 215                 220

```
Tyr His Ala Lys Ala Thr Glu His Leu Ser Thr Leu Ser Glu Lys Ala
225                 230                 235                 240

Lys Pro Ala Leu Glu Asp Leu Arg Gln Gly Leu Leu Pro Val Leu Glu
            245                 250                 255

Ser Phe Lys Val Ser Phe Leu Ser Ala Leu Glu Glu Tyr Thr Lys Lys
        260                 265                 270

Leu Asn Thr Gln
        275

<210> SEQ ID NO 8
<211> LENGTH: 220
<212> TYPE: PRT
<213> ORGANISM: Homo sapiens

<400> SEQUENCE: 8

Gly His His His His His His Asp Tyr Asp Ile Pro Thr Thr Glu
1               5                   10                  15

Asn Leu Tyr Phe Gln Gly Ser Thr Phe Ser Lys Leu Arg Glu Gln Leu
            20                  25                  30

Gly Pro Val Thr Gln Glu Phe Trp Asp Asn Leu Glu Lys Glu Thr Glu
        35                  40                  45

Gly Leu Arg Gln Glu Met Ser Lys Asp Leu Glu Glu Val Lys Ala Lys
50                  55                  60

Val Gln Pro Tyr Leu Asp Asp Phe Gln Lys Lys Trp Gln Glu Glu Met
65                  70                  75                  80

Glu Leu Tyr Arg Gln Lys Val Glu Pro Leu Arg Ala Glu Leu Gln Glu
                85                  90                  95

Gly Ala Arg Gln Lys Leu His Glu Leu Gln Glu Lys Leu Ser Pro Leu
            100                 105                 110

Gly Glu Glu Met Arg Asp Arg Ala Arg Ala His Val Asp Ala Leu Arg
        115                 120                 125

Thr His Leu Ala Pro Tyr Ser Asp Glu Leu Arg Gln Arg Leu Ala Ala
    130                 135                 140

Arg Leu Glu Ala Leu Lys Glu Asn Gly Gly Ala Arg Leu Ala Glu Tyr
145                 150                 155                 160

His Ala Lys Ala Thr Glu His Leu Ser Thr Leu Ser Glu Lys Ala Lys
                165                 170                 175

Pro Ala Leu Glu Asp Leu Arg Gln Gly Leu Leu Pro Val Leu Glu Ser
            180                 185                 190

Phe Lys Val Ser Phe Leu Ser Ala Leu Glu Glu Tyr Thr Lys Lys Leu
        195                 200                 205

Asn Thr Gln Gly Asp Tyr Lys Asp Asp Asp Lys
    210                 215                 220

<210> SEQ ID NO 9
<211> LENGTH: 220
<212> TYPE: PRT
<213> ORGANISM: Homo sapiens

<400> SEQUENCE: 9

Gly His His His His His His Asp Tyr Asp Ile Pro Thr Thr Glu
1               5                   10                  15

Asn Leu Tyr Phe Gln Gly Ser Asp Tyr Lys Asp Asp Asp Lys Thr
            20                  25                  30

Phe Ser Lys Leu Arg Glu Gln Leu Gly Pro Val Thr Gln Glu Phe Trp
        35                  40                  45
```

-continued

```
Asp Asn Leu Glu Lys Glu Thr Glu Gly Leu Arg Gln Glu Met Ser Lys
 50                  55                  60

Asp Leu Glu Glu Val Lys Ala Lys Val Gln Pro Tyr Leu Asp Asp Phe
 65                  70                  75                  80

Gln Lys Lys Trp Gln Glu Glu Met Glu Leu Tyr Arg Gln Lys Val Glu
                 85                  90                  95

Pro Leu Arg Ala Glu Leu Gln Glu Gly Ala Arg Gln Lys Leu His Glu
                100                 105                 110

Leu Gln Glu Lys Leu Ser Pro Leu Gly Glu Glu Met Arg Asp Arg Ala
            115                 120                 125

Arg Ala His Val Asp Ala Leu Arg Thr His Leu Ala Pro Tyr Ser Asp
        130                 135                 140

Glu Leu Arg Gln Arg Leu Ala Ala Arg Leu Glu Ala Leu Lys Glu Asn
145                 150                 155                 160

Gly Gly Ala Arg Leu Ala Glu Tyr His Ala Lys Ala Thr Glu His Leu
                165                 170                 175

Ser Thr Leu Ser Glu Lys Ala Lys Pro Ala Leu Glu Asp Leu Arg Gln
                180                 185                 190

Gly Leu Leu Pro Val Leu Glu Ser Phe Lys Val Ser Phe Leu Ser Ala
            195                 200                 205

Leu Glu Glu Tyr Thr Lys Lys Leu Asn Thr Gln Gly
210                 215                 220

<210> SEQ ID NO 10
<211> LENGTH: 391
<212> TYPE: PRT
<213> ORGANISM: Homo sapiens

<400> SEQUENCE: 10

Gly His His His His His His Asp Tyr Asp Ile Pro Thr Thr Glu
 1               5                  10                  15

Asn Leu Tyr Phe Gln Gly Ser Thr Phe Ser Lys Leu Arg Glu Gln Leu
                 20                  25                  30

Gly Pro Val Thr Gln Glu Phe Trp Asp Asn Leu Glu Lys Glu Thr Glu
             35                  40                  45

Gly Leu Arg Gln Glu Met Ser Lys Asp Leu Glu Glu Val Lys Ala Lys
 50                  55                  60

Val Gln Pro Tyr Leu Asp Asp Phe Gln Lys Lys Trp Gln Glu Glu Met
 65                  70                  75                  80

Glu Leu Tyr Arg Gln Lys Val Glu Pro Leu Arg Ala Glu Leu Gln Glu
                 85                  90                  95

Gly Ala Arg Gln Lys Leu His Glu Leu Gln Glu Lys Leu Ser Pro Leu
                100                 105                 110

Gly Glu Glu Met Arg Asp Arg Ala Arg Ala His Val Asp Ala Leu Arg
            115                 120                 125

Thr His Leu Ala Pro Tyr Ser Asp Glu Leu Arg Gln Arg Leu Ala Ala
        130                 135                 140

Arg Leu Glu Ala Leu Lys Glu Asn Gly Gly Ala Arg Leu Ala Glu Tyr
145                 150                 155                 160

His Ala Lys Ala Thr Glu His Leu Ser Thr Leu Ser Glu Lys Ala Lys
                165                 170                 175

Pro Ala Leu Glu Asp Leu Arg Gln Gly Leu Leu Pro Val Leu Glu Ser
                180                 185                 190

Phe Lys Val Ser Phe Leu Ser Ala Leu Glu Glu Tyr Thr Lys Lys Leu
```

-continued

```
                195                 200                 205
Asn Thr Gln Gly Thr Pro Val Thr Gln Glu Phe Trp Asp Asn Leu Glu
210                 215                 220

Lys Glu Thr Glu Gly Leu Arg Gln Glu Met Ser Lys Asp Leu Glu Glu
225                 230                 235                 240

Val Lys Ala Lys Val Gln Pro Tyr Leu Asp Asp Phe Gln Lys Lys Trp
                245                 250                 255

Gln Glu Glu Met Glu Leu Tyr Arg Gln Lys Val Glu Pro Leu Arg Ala
                260                 265                 270

Glu Leu Gln Glu Gly Ala Arg Gln Lys Leu His Glu Leu Gln Glu Lys
                275                 280                 285

Leu Ser Pro Leu Gly Glu Glu Met Arg Asp Arg Ala Arg Ala His Val
290                 295                 300

Asp Ala Leu Arg Thr His Leu Ala Pro Tyr Ser Asp Glu Leu Arg Gln
305                 310                 315                 320

Arg Leu Ala Ala Arg Leu Glu Ala Leu Lys Glu Asn Gly Gly Ala Arg
                325                 330                 335

Leu Ala Glu Tyr His Ala Lys Ala Thr Glu His Leu Ser Thr Leu Ser
                340                 345                 350

Glu Lys Ala Lys Pro Ala Leu Glu Asp Leu Arg Gln Gly Leu Leu Pro
                355                 360                 365

Val Leu Glu Ser Phe Lys Val Ser Phe Leu Ser Ala Leu Glu Glu Tyr
                370                 375                 380

Thr Lys Lys Leu Asn Thr Gln
385                 390

<210> SEQ ID NO 11
<211> LENGTH: 231
<212> TYPE: PRT
<213> ORGANISM: Homo sapiens
<220> FEATURE:
<221> NAME/KEY: Optionally_Biotinylated
<222> LOCATION: (231)..(231)

<400> SEQUENCE: 11

Gly His His His His His His Asp Tyr Asp Ile Pro Thr Thr Glu
1               5                   10                  15

Asn Leu Tyr Phe Gln Gly Ser Thr Phe Ser Lys Leu Arg Glu Gln Leu
                20                  25                  30

Gly Pro Val Thr Gln Glu Phe Trp Asp Asn Leu Glu Lys Glu Thr Glu
                35                  40                  45

Gly Leu Arg Gln Glu Met Ser Lys Asp Leu Glu Glu Val Lys Ala Lys
                50                  55                  60

Val Gln Pro Tyr Leu Asp Asp Phe Gln Lys Lys Trp Gln Glu Glu Met
65                  70                  75                  80

Glu Leu Tyr Arg Gln Lys Val Glu Pro Leu Arg Ala Glu Leu Gln Glu
                85                  90                  95

Gly Ala Arg Gln Lys Leu His Glu Leu Gln Glu Lys Leu Ser Pro Leu
                100                 105                 110

Gly Glu Glu Met Arg Asp Arg Ala Arg Ala His Val Asp Ala Leu Arg
                115                 120                 125

Thr His Leu Ala Pro Tyr Ser Asp Glu Leu Arg Gln Arg Leu Ala Ala
                130                 135                 140

Arg Leu Glu Ala Leu Lys Glu Asn Gly Gly Ala Arg Leu Ala Glu Tyr
145                 150                 155                 160
```

His Ala Lys Ala Thr Glu His Leu Ser Thr Leu Ser Glu Lys Ala Lys
                165                 170                 175

Pro Ala Leu Glu Asp Leu Arg Gln Gly Leu Leu Pro Val Leu Glu Ser
            180                 185                 190

Phe Lys Val Ser Phe Leu Ser Ala Leu Glu Glu Tyr Thr Lys Lys Leu
        195                 200                 205

Asn Thr Gln Ser Leu Leu Gly Gly Leu Asn Asp Ile Phe Glu Ala
    210                 215                 220

Gln Lys Ile Glu Trp His Glu
225                 230

<210> SEQ ID NO 12
<211> LENGTH: 211
<212> TYPE: PRT
<213> ORGANISM: Homo sapiens

<400> SEQUENCE: 12

Gly His His His His His His Asp Tyr Asp Ile Pro Thr Thr Glu
1               5                   10                  15

Asn Leu Tyr Phe Gln Gly Ser Thr Phe Ser Lys Leu Arg Glu Gln Leu
            20                  25                  30

Gly Pro Val Thr Gln Glu Phe Phe Asp Asn Leu Glu Lys Glu Thr Glu
        35                  40                  45

Gly Leu Arg Gln Glu Met Ser Lys Asp Leu Glu Val Lys Ala Lys
    50                  55                  60

Val Gln Pro Tyr Leu Asp Asp Phe Gln Lys Lys Phe Gln Glu Met
65                  70                  75                  80

Glu Leu Tyr Arg Gln Lys Val Glu Pro Leu Arg Ala Glu Leu Gln Glu
                85                  90                  95

Gly Ala Arg Gln Lys Leu His Glu Leu Gln Glu Lys Leu Ser Pro Leu
            100                 105                 110

Gly Glu Glu Met Arg Asp Arg Ala Arg Ala His Val Asp Ala Leu Arg
        115                 120                 125

Thr His Leu Ala Pro Tyr Ser Asp Glu Leu Arg Gln Arg Leu Ala Ala
    130                 135                 140

Arg Leu Glu Ala Leu Lys Glu Asn Gly Gly Ala Arg Leu Ala Glu Tyr
145                 150                 155                 160

His Ala Lys Ala Thr Glu His Leu Ser Thr Leu Ser Glu Lys Ala Lys
                165                 170                 175

Pro Ala Leu Glu Asp Leu Arg Gln Gly Leu Leu Pro Val Leu Glu Ser
            180                 185                 190

Phe Lys Val Ser Phe Leu Ser Ala Leu Glu Glu Tyr Thr Lys Lys Leu
        195                 200                 205

Asn Thr Gln
    210

<210> SEQ ID NO 13
<211> LENGTH: 167
<212> TYPE: PRT
<213> ORGANISM: Homo sapiens

<400> SEQUENCE: 13

Gly His His His His His His Asp Tyr Asp Ile Pro Thr Thr Glu
1               5                   10                  15

Asn Leu Tyr Phe Gln Gly Ser Thr Phe Ser Lys Leu Arg Glu Gln Leu
            20                  25                  30

```
Gly Pro Val Thr Gln Glu Phe Trp Asp Asn Leu Glu Lys Glu Thr Glu
            35                  40                  45

Gly Leu Arg Gln Glu Met Ser Lys Asp Leu Glu Val Lys Ala Lys
 50                  55                  60

Val Gln Pro Leu Gly Glu Met Arg Asp Arg Ala Arg Ala His Val
 65                  70                  75                  80

Asp Ala Leu Arg Thr His Leu Ala Pro Tyr Ser Asp Glu Leu Arg Gln
                85                  90                  95

Arg Leu Ala Ala Arg Leu Glu Ala Leu Lys Glu Asn Gly Gly Ala Arg
                100                 105                 110

Leu Ala Glu Tyr His Ala Lys Ala Thr Glu His Leu Ser Thr Leu Ser
                115                 120                 125

Glu Lys Ala Lys Pro Ala Leu Glu Asp Leu Arg Gln Gly Leu Leu Pro
130                 135                 140

Val Leu Glu Ser Phe Lys Val Ser Phe Leu Ser Ala Leu Glu Glu Tyr
145                 150                 155                 160

Thr Lys Lys Leu Asn Thr Gln
                165

<210> SEQ ID NO 14
<211> LENGTH: 243
<212> TYPE: PRT
<213> ORGANISM: Homo sapiens

<400> SEQUENCE: 14

Asp Glu Pro Pro Gln Ser Pro Trp Asp Arg Val Lys Asp Leu Ala Thr
 1               5                  10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
                35                  40                  45

Asn Trp Asp Ser Val Thr Ser Thr Phe Ser Lys Leu Arg Glu Gln Leu
 50                  55                  60

Gly Pro Val Thr Gln Glu Phe Trp Asp Asn Leu Glu Lys Glu Thr Glu
 65                  70                  75                  80

Gly Leu Arg Gln Glu Met Ser Lys Asp Leu Glu Val Lys Ala Lys
                85                  90                  95

Val Gln Pro Tyr Leu Asp Asp Phe Gln Lys Lys Trp Gln Glu Glu Met
                100                 105                 110

Glu Leu Tyr Arg Gln Lys Val Glu Pro Leu Arg Ala Glu Leu Gln Glu
                115                 120                 125

Gly Ala Arg Gln Lys Leu His Glu Leu Gln Glu Lys Leu Ser Pro Leu
                130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
                180                 185                 190

His Ala Lys Ala Thr Glu His Leu Ser Thr Leu Ser Glu Lys Ala Lys
                195                 200                 205

Pro Ala Leu Glu Asp Leu Arg Gln Gly Leu Leu Pro Val Leu Glu Ser
                210                 215                 220

Phe Lys Val Ser Phe Leu Ser Ala Leu Glu Glu Tyr Thr Lys Lys Leu
225                 230                 235                 240
```

Asn Thr Gln

<210> SEQ ID NO 15
<211> LENGTH: 326
<212> TYPE: PRT
<213> ORGANISM: Ebola virus

<400> SEQUENCE: 15

Met Arg Arg Val Ile Leu Pro Thr Ala Pro Pro Glu Tyr Met Glu Ala
1               5                   10                  15

Ile Tyr Pro Val Arg Ser Asn Ser Thr Ile Ala Arg Gly Gly Asn Ser
            20                  25                  30

Asn Thr Gly Phe Leu Thr Pro Glu Ser Val Asn Gly Asp Thr Pro Ser
        35                  40                  45

Asn Pro Leu Arg Pro Ile Ala Asp Asp Thr Ile Asp His Ala Ser His
    50                  55                  60

Thr Pro Gly Ser Val Ser Ser Ala Phe Ile Leu Glu Ala Met Val Asn
65                  70                  75                  80

Val Ile Ser Gly Pro Lys Val Leu Met Lys Gln Ile Pro Ile Trp Leu
                85                  90                  95

Pro Leu Gly Val Ala Asp Gln Lys Thr Tyr Ser Phe Asp Ser Thr Thr
            100                 105                 110

Ala Ala Ile Met Leu Ala Ser Tyr Thr Ile Thr His Phe Gly Lys Ala
        115                 120                 125

Thr Asn Pro Leu Val Arg Val Asn Arg Leu Gly Pro Gly Ile Pro Asp
    130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
            180                 185                 190

Asp Asp Thr Pro Thr Gly Ser Asn Gly Ala Leu Arg Pro Gly Ile Ser
        195                 200                 205

Phe His Pro Lys Leu Arg Pro Ile Leu Leu Pro Asn Lys Ser Gly Lys
    210                 215                 220

Lys Gly Asn Ser Ala Asp Leu Thr Ser Pro Glu Lys Ile Gln Ala Ile
225                 230                 235                 240

Met Thr Ser Leu Gln Asp Phe Lys Ile Val Pro Ile Asp Pro Thr Lys
                245                 250                 255

Asn Ile Met Gly Ile Glu Val Pro Glu Thr Leu Val His Lys Leu Thr
            260                 265                 270

Gly Lys Lys Val Thr Ser Lys Asn Gly Gln Pro Ile Ile Pro Val Leu
        275                 280                 285

Leu Pro Lys Tyr Ile Gly Leu Asp Pro Val Ala Pro Gly Asp Leu Thr
    290                 295                 300

Met Val Ile Thr Gln Asp Cys Asp Thr Cys His Ser Pro Ala Ser Leu
305                 310                 315                 320

Pro Ala Val Ile Glu Lys
                325

<210> SEQ ID NO 16
<211> LENGTH: 676
<212> TYPE: PRT
<213> ORGANISM: Ebola virus

<400> SEQUENCE: 16

```
Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Ser Leu Thr Thr Lys Pro Gly Pro
    370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
```

```
                        405                 410                 415
Ala Ser Asp Thr Pro Ser Ala Thr Thr Ala Ala Gly Pro Pro Lys Ala
                420                 425                 430

Glu Asn Thr Asn Thr Ser Lys Ser Thr Asp Phe Leu Asp Pro Ala Thr
            435                 440                 445

Thr Thr Ser Pro Gln Asn His Ser Glu Thr Ala Gly Asn Asn Asn Thr
        450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 17
<211> LENGTH: 276
<212> TYPE: PRT
<213> ORGANISM: Unknown
<220> FEATURE:
<223> OTHER INFORMATION: Zika Virus

<400> SEQUENCE: 17

Phe Thr Cys Ser Arg Lys Met Thr Gly Lys Ser Ile Gln Pro Glu Asn
1               5                   10                  15

Leu Glu Tyr Arg Ile Met Leu Ser Val His Gly Ser Gln His Ser Gly
            20                  25                  30

Met Ile Val Asn Asp Glu Asn Arg Ala Lys Val Glu Val Thr Pro Asn
        35                  40                  45

Ser Pro Arg Ala Glu Ala Thr Leu Gly Gly Phe Gly Ser Leu Gly Leu
    50                  55                  60

Asp Cys Glu Pro Arg Thr Gly Leu Asp Phe Ser Asp Leu Tyr Tyr Leu
65                  70                  75                  80

Thr Met Asn Asn Lys His Trp Leu Val His Lys Glu Trp Phe His Asp
```

```
                85                  90                  95
Ile Pro Leu Pro Trp His Ala Gly Ala Asp Thr Gly Thr Pro His Trp
            100                 105                 110

Asn Asn Lys Glu Ala Leu Val Glu Phe Lys Asp Ala His Ala Lys Arg
        115                 120                 125

Gln Thr Val Val Val Leu Gly Ser Gln Glu Gly Ala Val His Thr Ala
    130                 135                 140

Leu Ala Gly Ala Leu Glu Ala Glu Met Asp Gly Ala Lys Gly Arg Leu
145                 150                 155                 160

Ser Ser Gly His Leu Lys Cys Arg Leu Lys Met Asp Lys Leu Arg Leu
                165                 170                 175

Glu Gly Val Ser Tyr Ser Leu Cys Thr Ala Ala Phe Thr Phe Thr Lys
            180                 185                 190

Val Pro Ala Glu Thr Leu His Gly Thr Val Thr Val Glu Val Gln Tyr
        195                 200                 205

Ala Gly Thr Asp Gly Pro Cys Lys Val Pro Ala Gln Met Ala Val Asp
    210                 215                 220

Met Gln Thr Leu Thr Pro Val Gly Arg Leu Ile Thr Ala Asn Pro Val
225                 230                 235                 240

Ile Thr Glu Ser Thr Glu Asn Ser Lys Met Met Leu Glu Leu Asp Pro
                245                 250                 255

Pro Phe Gly Asp Ser Tyr Ile Val Ile Gly Val Gly Asp Lys Lys Ile
            260                 265                 270

Thr His His Trp
        275

<210> SEQ ID NO 18
<211> LENGTH: 565
<212> TYPE: PRT
<213> ORGANISM: Influenza A virus

<400> SEQUENCE: 18

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175
```

-continued

Leu Lys Asn Ser Tyr Val Asn Lys Lys Gly Lys Glu Val Leu Val Leu
            180                 185                 190

Trp Gly Ile His His Pro Asn Ser Lys Glu Gln Gln Asn Leu Tyr
        195                 200                 205

Gln Asn Glu Asn Ala Tyr Val Ser Val Val Thr Ser Asn Tyr Asn Arg
210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

We claim:

1. A thermostable vaccine carrier, comprising a bilayer comprising one or more ether glycerophospholipids and one or more membrane scaffold proteins self-assembled into a nanodisc, and a microbial protein antigen embedded into the nanodisc.

2. The thermostable vaccine carrier according to claim 1, wherein the one or more ether glycerophospholipids is selected from the group consisting of 1,2-di-O-phytanyl-sn-glycero-3-phosphocholine, 1,2-di-O-phytanyl-sn-glycero-3-phosphoethanolamine, glycerol dialkyl glycerol tetraether, 1,2-di-O-octadecyl-sn-glycero-3-phosphocholine, 1,2-di-O-(9Z-octadecenyl)-sn-glycero-3-phosphocholine, 2-3-diphytanyl-O-sn-glycerol (archaeol), caldarcheol, isocalarcheol, gentiobiosyl archaeol, archaetidylethanoloamine, gentyobiosyl caldarc haetidylethanoloamine, and combinations thereof.

3. The thermostable vaccine carrier according to claim 1, wherein the one or more ether glycerophospholipids comprises 1,2-di-O-phytanyl-sn-glycero-3-phosphocholine, 1,2-di-O-phytanyl-sn-glycero-3-phosphoethanolamine, or glycerol dialkyl glycerol tetraether.

4. The thermostable vaccine carrier according to claim 1, wherein the membrane scaffold protein comprises a human apolipoprotein A1 fragment peptide or a variant thereof having one amino acid substitution or deletion.

5. The thermostable vaccine carrier according to claim 1, wherein the membrane scaffold protein has the amino acid sequence of SEQ ID NO:1.

6. The thermostable vaccine carrier according to claim 1, wherein the human apolipoprotein A1 fragment peptide has an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13.

7. The thermostable vaccine carrier according to claim 1, wherein the microbial protein antigen is a virus envelope protein.

8. The thermostable vaccine carrier according to claim 1, wherein the microbial protein antigen is a virus envelope protein, and the virus is a DNA virus.

9. The thermostable vaccine carrier according to claim 8, wherein the DNA virus is a herpesvirus, poxsvirus, or hepadnavirus.

10. The thermostable vaccine carrier according to claim 1, wherein the microbial protein antigen is a virus envelope protein, and the virus is an RNA virus.

11. The thermostable vaccine carrier according to claim 10, wherein the RNA virus is a togavirus, coronavirus, orthomyxovirus, paramyxovirus, rhabdovirus, bunyavirus, filovirus, or flavivirus.

12. The thermostable vaccine carrier according to claim 11, wherein the orthomyxovirus is an Influenza virus.

13. The thermostable vaccine carrier according to claim 11, wherein the filovirus is Ebola virus.

14. The thermostable vaccine carrier according to claim 11, wherein the flavivirus is Zika virus.

15. A composition, comprising the thermostable vaccine carrier according to claim 1 and a pharmaceutically acceptable carrier.

16. A kit, comprising the thermostable vaccine carrier according to claim 1, a container containing the carrier, and instructions for using the carrier in a method for vaccinating a subject in need thereof.

17. A method for vaccinating a subject in need thereof, comprising administering to the subject the thermostable vaccine carrier according to claim 1 in an amount effective to confer an immune response against the microbial protein antigen in the subject.

18. A method for making thermostable vaccine carrier according to claim 1, comprising mixing the one or more ether glycerophospholipids, the one or more membrane scaffold proteins, and the microbial protein antigen in an aqueous media comprising a detergent, removing the detergent, and allowing the one or more membrane scaffold proteins and the one or more ether glycerophospholipids to self-assemble into the nanodisc having the microbial protein antigen embedded therein.

* * * * *